(12) United States Patent
Singh et al.

(10) Patent No.: US 8,898,885 B2
(45) Date of Patent: Dec. 2, 2014

(54) METHOD FOR MANUFACTURE OF MULTI-LAYER-MULTI-TURN STRUCTURE FOR HIGH EFFICIENCY WIRELESS COMMUNICATION

(75) Inventors: Vinit Singh, Austin, TX (US); Christine A. Frysz, Orchard Park, NY (US); Matthew Geary, Chicago, IL (US); Eitan Babcock, Milwaukee, WI (US); Justin Derbas, Orland Park, IL (US)

(73) Assignee: NuCurrent, Inc., Chicago, IL (US)

( * ) Notice: Subject to any disclaimer, the term of this patent is extended or adjusted under 35 U.S.C. 154(b) by 0 days.

(21) Appl. No.: 13/233,735

(22) Filed: Sep. 15, 2011

(65) Prior Publication Data

US 2013/0067738 A1    Mar. 21, 2013

Related U.S. Application Data

(63) Continuation-in-part of application No. 13/255,659, filed as application No. PCT/US2010/000714 on Mar. 9, 2010, now Pat. No. 8,855,786.

(60) Provisional application No. 61/158,688, filed on Mar. 9, 2009.

(51) Int. Cl.
*H04R 31/00* (2006.01)
*H01Q 7/00* (2006.01)
*A61N 1/372* (2006.01)

(52) U.S. Cl.
CPC .............. *H01Q 7/00* (2013.01); *A61N 1/37229* (2013.01)
USPC ................ 29/594; 29/609.1; 29/825; 29/846; 336/200; 336/232; 438/674

(58) Field of Classification Search
USPC .......... 29/592.1, 594, 595, 602.1; 216/62, 65, 216/66; 361/283, 301; 73/504.02, 504.04, 73/504.12–504.16; 438/674; 336/200, 232
See application file for complete search history.

(56) References Cited

U.S. PATENT DOCUMENTS

| | | | |
|---|---|---|---|
| 2,911,605 A | 11/1959 | Wales, Jr. | |
| 3,484,731 A | 12/1969 | Rich | |
| 4,328,531 A * | 5/1982 | Nagashima et al. | 361/762 |
| 4,494,100 A | 1/1985 | Stengel et al. | |
| 4,959,631 A * | 9/1990 | Hasegawa et al. | 336/83 |
| 4,996,165 A * | 2/1991 | Chang et al. | 438/699 |
| 5,237,165 A | 8/1993 | Tingley, III | |
| 5,604,352 A | 2/1997 | Schuetz | |
| 5,713,939 A | 2/1998 | Nedungadi et al. | |

(Continued)

FOREIGN PATENT DOCUMENTS

| | | |
|---|---|---|
| EP | 1609503 A1 | 12/2005 |
| EP | 2031729 A2 | 3/2009 |

OTHER PUBLICATIONS

European Search Report dated Aug. 7, 2014 for European Patent Application No. 10751119.8.

*Primary Examiner* — Paul D Kim
(74) *Attorney, Agent, or Firm* — McDermott Will & Emery LLP

(57) ABSTRACT

A structure for wireless communication having a plurality of conductor layers, an insulator layer separating each of the conductor layers, and at least one connector connecting two of the conductor layers wherein an electrical resistance is reduced when an electrical signal is induced in the resonator at a predetermined frequency.

21 Claims, 26 Drawing Sheets

(56) References Cited

U.S. PATENT DOCUMENTS

| | | | |
|---|---|---|---|
| 5,748,464 A | 5/1998 | Schuetz | |
| 5,777,538 A | 7/1998 | Schuetz | |
| 5,801,611 A | 9/1998 | Van Loenen et al. | |
| 5,838,154 A * | 11/1998 | Morikawa et al. | 324/249 |
| 5,883,392 A | 3/1999 | Schuetz | |
| 6,503,831 B2 | 1/2003 | Speakman | |
| 6,664,863 B1 | 12/2003 | Okamoto et al. | |
| 6,809,688 B2 * | 10/2004 | Yamada | 343/700 MS |
| 6,924,230 B2 * | 8/2005 | Sun et al. | 438/640 |
| 7,046,113 B1 | 5/2006 | Okamoto et al. | |
| 7,205,655 B2 | 4/2007 | Sippola | |
| 7,563,352 B2 * | 7/2009 | Hubel | 205/82 |
| 7,713,762 B2 * | 5/2010 | Lee et al. | 438/14 |
| 7,786,836 B2 | 8/2010 | Gabara | |
| 7,952,365 B2 * | 5/2011 | Narita et al. | 324/633 |
| 8,056,819 B2 | 11/2011 | Rowell et al. | |
| 8,567,048 B2 * | 10/2013 | Singh et al. | 29/825 |
| 2002/0105080 A1 | 8/2002 | Speakman | |
| 2003/0119677 A1 | 6/2003 | Qiyan et al. | |
| 2004/0000974 A1 | 1/2004 | Odenaal et al. | |
| 2007/0023424 A1 | 2/2007 | Weber | |
| 2008/0211320 A1 | 9/2008 | Cook et al. | |
| 2009/0015266 A1 * | 1/2009 | Narita et al. | 324/603 |
| 2009/0152542 A1 * | 6/2009 | Lee et al. | 257/48 |
| 2009/0261936 A1 * | 10/2009 | Widjaja et al. | 336/200 |
| 2010/0033290 A1 | 2/2010 | Liu et al. | |
| 2011/0248891 A1 * | 10/2011 | Han et al. | 343/700 MS |
| 2012/0235500 A1 | 9/2012 | Ganem et al. | |
| 2012/0235634 A1 | 9/2012 | Hall et al. | |

* cited by examiner

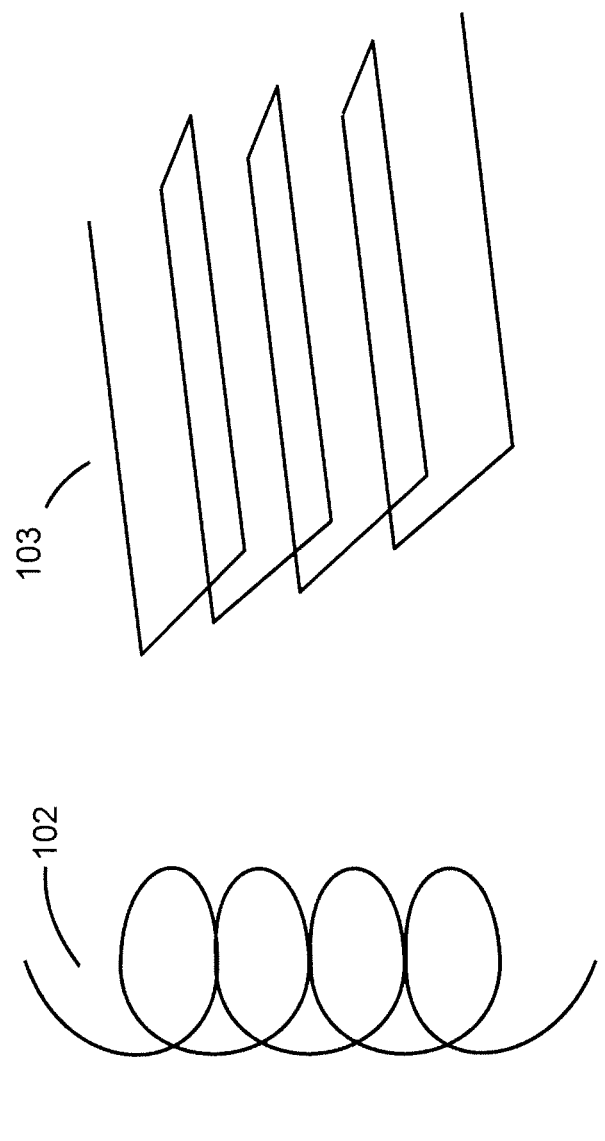

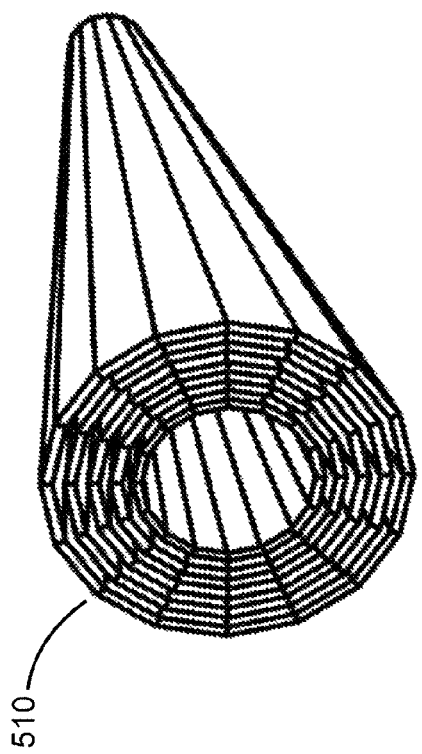
FIG. 8A
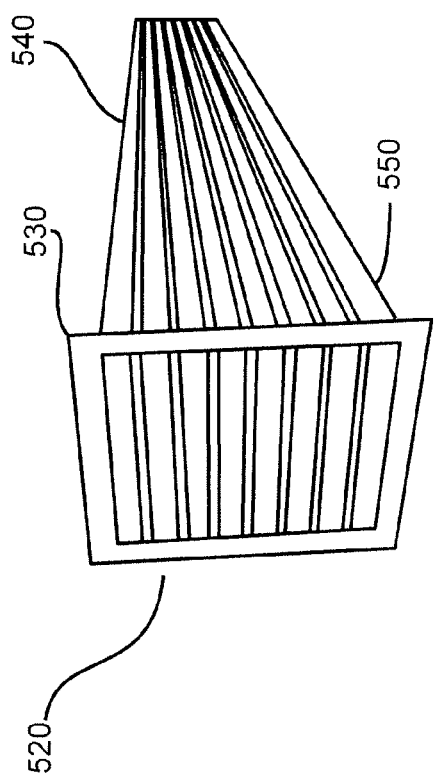
FIG. 8B
FIG. 7E
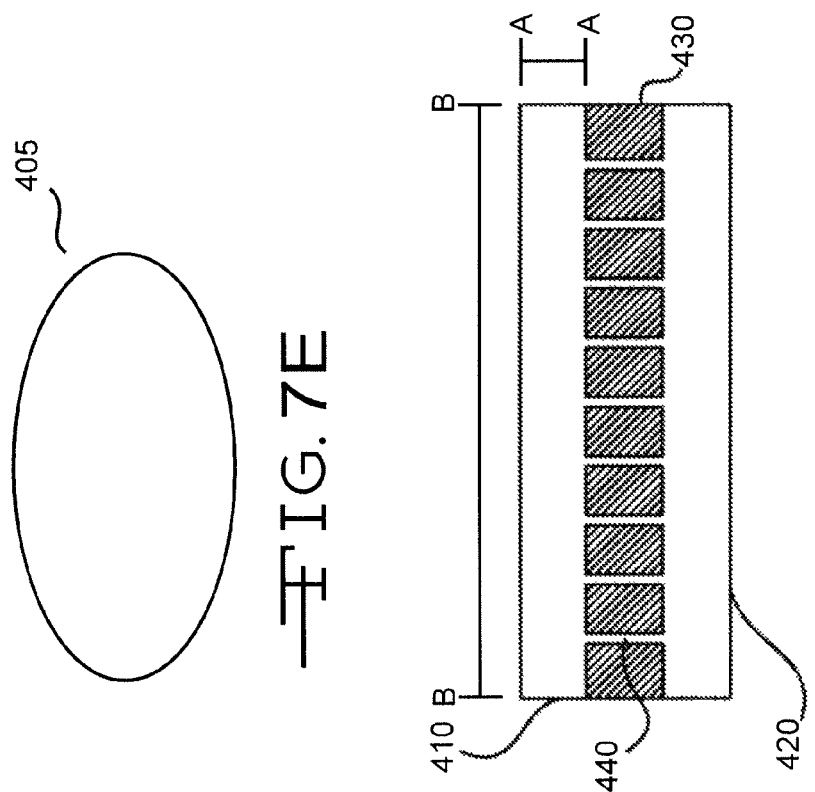
FIG. 7F

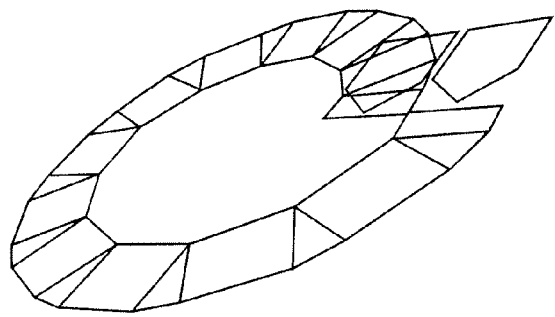
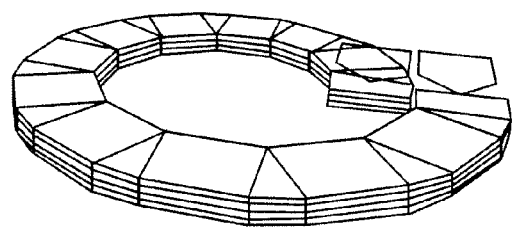
FIG. 9A  FIG. 9B
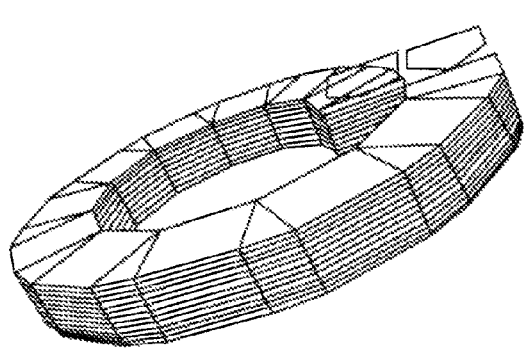
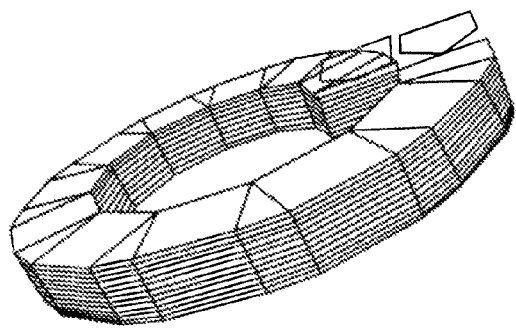
FIG. 9C  FIG. 9D

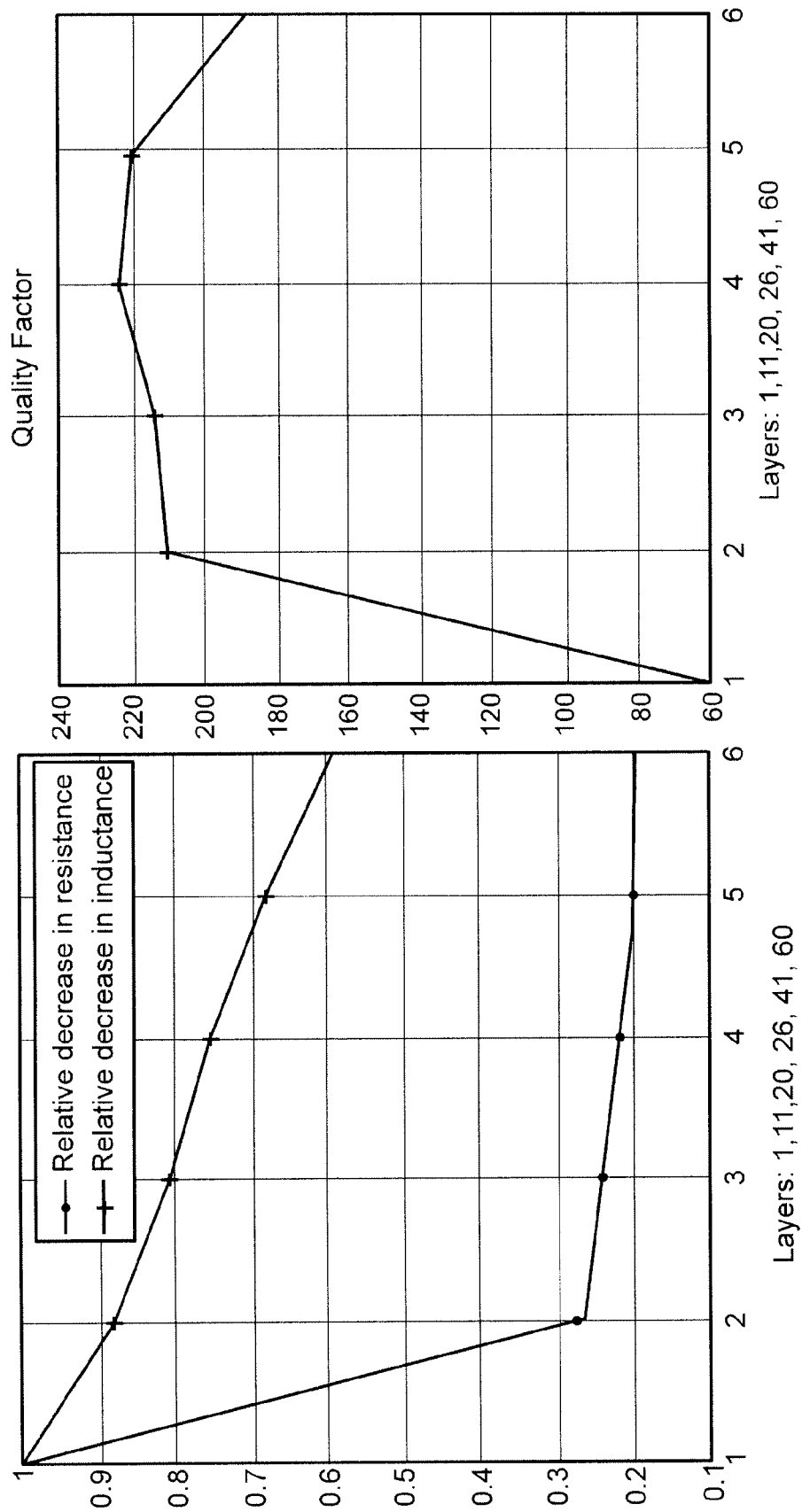

When MLMT is in Mode 2a

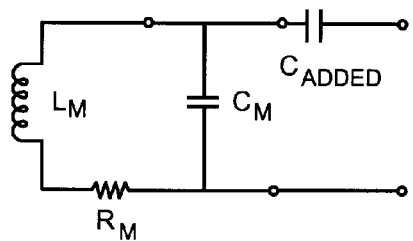
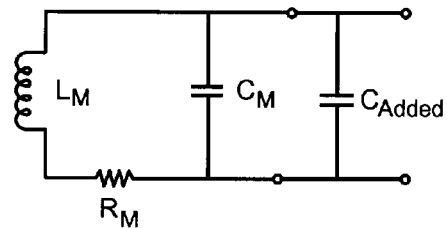
FIG. 23A          FIG. 23B
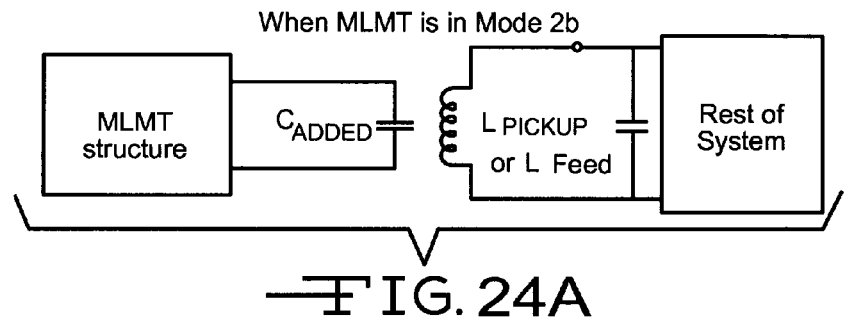
FIG. 24A
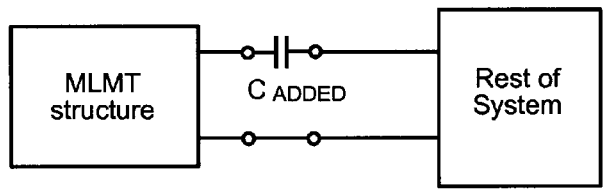
FIG. 24B
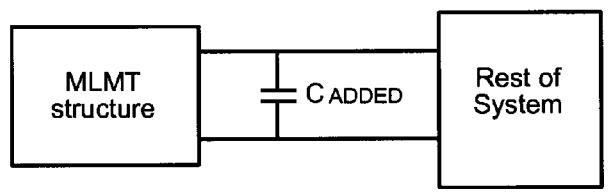
FIG. 24C

METHOD FOR MANUFACTURE OF MULTI-LAYER-MULTI-TURN STRUCTURE FOR HIGH EFFICIENCY WIRELESS COMMUNICATION

RELATED APPLICATIONS

This application is a continuation in part of U.S. application Ser. No. 13/255,659 entitled "System and Method for Wireless Power Transfer in Implantable Medical Devices," filed on Sep. 9, 2011, with a 371(c) date of Nov. 22, 2011, which claims priority to International Application No. PCT/US2010/000714 entitled "System and Method for Wireless Power Transfer in Implantable Medical Devices," filed on Mar. 9, 2010, which claims priority to U.S. Provisional Application No. 61/158,688, filed on Mar. 9, 2009, the disclosures of which are entirely incorporated herein by reference.

The present patent application also hereby incorporates by reference the entire contents of U.S. patent application Ser. No. 13/233,538, now U.S. Publication No. 2013/0069843, filed on Sep. 15, 2011; U.S. patent application Ser. No. 13/233,569, now U.S. Publication No. 2013/0069748, filed on Sep. 15, 2011; U.S. patent application Ser. No. 13/233,624, now U.S. Pat. No. 8,653,927, filed on Sep. 15, 2011; U.S. patent application Ser. No. 13/233,633, now U.S. Pat. No. 8,814,025, filed on Sep. 15, 2011; U.S. patent application Ser. No. 13/233,686, now U.S. Pat. No. 8,567,048, filed on Sep. 15, 2011; U.S. patent application Ser. No. 13/233,707, now U.S. Publication No. 2013/0068499, filed on Sep. 15, 2011; and U.S. patent application Ser. No. 13/233,751, now U.S. Publication No. 2013/0068507, filed on Sep. 15, 2011.

TECHNICAL FIELD

The present subject matter generally relates to methods, systems and apparatus to design, operate and manufacture wireless power and/or data transmission and/or communication systems, and more specifically, to methods, systems and apparatus to design, operate and manufacture a high efficiency structure for use in near-field wireless power and/or data transmission and/or communication systems.

BACKGROUND

In recent years, applications employing near-field wireless power and/or data transmission and/or communication systems, such as commercial electronics, medical systems, military systems, high frequency transformers, microelectronics including nanoscale power and/or data transfer or microelectromechanical systems (MEMS) thereof, industrial, scientific and medical (ISM) band receivers, wireless sensing and the like, have been limited in achieving optimal performance because the antennas (also referred to as resonators) utilized in these systems have relatively low quality factors.

The relatively low quality factors of these wireless transmission and/or communication systems are mainly due to higher resistive losses caused by a phenomenon known as the "skin effect." Generally, skin effect is the tendency of an alternating electric current (AC) to distribute itself within a conductor such that the current density is more predominant near the surface of the conductor with the remaining conductor body 'unused' relative to electrical current flow. The remaining conductor body is 'unused' relative to electrical current flow because the current density typically decays with distance therewithin away from the surface of the conductor. The electric current flows mostly near the surface, and is referred to as the "skin" of the conductor. The depth at which current flows from the surface is referred to as the "skin depth." The "skin depth" then defines the electrical signal conducting path that is active in transmission and/or communication, while the conductor is defined as the body that is capable of conducting an electrical signal.

In systems employing wireless power and/or data transmission and/or communication, the skin effect phenomenon generally causes energy loss as current flows through the antenna wire and circuit. Higher resistive loss at high frequencies is a problem faced by most electronic devices or appliances. Skin effect becomes more prevalent when operating frequency increases. With higher frequencies, current that normally flows through the entire cross section of the wire forming the antenna becomes restricted to its surface. As a result, the effective resistance of the wire is similar to that of a thinner wire rather than of the actual diameter through which the current could be distributed. A wire exhibiting tolerable resistance for efficient performance at low frequency transitions into a wire of unacceptable resistance at high frequency. The transition from tolerable to unacceptable resistance translates into an inefficient power and/or data transmission and/or communication system that is unable to conduct an electrical signal as needed in particular applications. Additionally, today's antenna designs do not resolve these inefficiencies, and, in some cases, exacerbate the inefficiencies of a wireless power and/or data transmission and/or communication system. Although not exhaustive, typical applications limited by current antenna technology include, for example, radio frequency identification (RFID), battery charging and recharging, telemetry, sensing, communication, asset tracking, patient monitoring, data entry and/or retrieval and the like. Overheating of system components, rate and accuracy of data retrieval, rate of energy delivery, transmission distance constraints, and transmission misalignment limitations are other serious problems in wireless power and/or data transmission and/or communication applications.

In applications of Implanted Medical Devices (IMDs), such as pacemakers, defibrillators and neuromodulation or neuromuscular stimulation devices, there is a desire to minimize battery recharge time. Faster battery recharge time reduces, for example, patient duration of discomfort, inconvenience, and potential for injury. If antennas have less resistive losses, battery recharge could be accomplished from greater distances and with higher tolerance to antenna misalignment or disorientation without compromising performance. Precise orientation and alignment is known to be difficult to achieve, especially for obese patients. Additionally, and/or alternatively, if structures of smaller sizes can be designed and practically manufactured while maintaining the performance characteristics required for successful system operation, then the overall dimensions of IMD's could be decreased.

In RFID applications, such as supply chain management, product authenticity, and asset tracking, there is a need to increase read range, increase read rates, improve system reliability and improve system accuracy. At high frequency for example, read range is at most three feet which is generally insufficient for pallet tracking. Ultra high frequency readers enable greater read distances of eight to ten feet, however, they introduce other performance issues like signals that are reflected by metal or are absorbed by water, or display unreadable, null spots in read fields. Increased read range requires concentrated power to facilitate reflecting back the signal for better performance, hence, a more efficient structure could help solve these issues.

In applications requiring efficient low loss coils which need to maintain resonance under harsh conditions, conventional wire-based antennas could be deformed. It is well known that any deformation of the wire cross-section will lead to a change in inductance and possibly resistance, which in turn will change the resonance frequency of the antenna and consequently may increase overall system resistance. Improved methods of manufacturing these types of structures that reduce the potential for compromising deformation could eliminate this problem. The present teachings include methods of manufacture that include both rigid structure designs and fixed flexible structure designs.

Litz wires were developed, in part, in an attempt to address the issues discussed above. However, Litz wires are generally insufficient for use in high frequency applications, and are therefore generally not useful in applications having operating frequencies above about 3 MHz. A Litz wire is a wire consisting of a number of individually insulated magnet wires twisted or braided into a uniform pattern, so that each wire strand tends to take all possible positions in the cross-section of the entire conductor. This multi-strand configuration or Litz construction is designed to minimize the power losses exhibited in solid conductors due to "skin effect". Litz wire constructions attempt to counteract this effect by increasing the amount of surface area without significantly increasing the size of the conductor. However, even properly constructed Litz wires exhibit some skin effect due to the limitations of stranding. Wires intended for higher frequency ranges generally require more strands of a finer gauge size than Litz wires of equal cross-sectional area but composed of fewer and larger strands. The highest frequency at which providers of Litz wires offer configurations capable of improving efficiencies is about 3 MHz. There is currently no solution for applications with operating frequencies beyond this 3 MHz maximum frequency limit.

Hence a need exists for an improved high efficiency structure design and method of manufacture that reduces the intrinsic resistive losses of the structure, and in particular reduces intrinsic resistive losses of the structure at high frequencies to achieve high quality factors.

SUMMARY

The teachings herein alleviate one or more of the above noted problems of higher resistive losses at high frequencies resulting in lower quality factors by utilizing the multi-layer wire concept to increase the area of conductance within a structure. The multi-layer wire configuration results in a reduction of conductor loss and an increase in the qualify factor of the structure. The present teachings apply to wireless transmission and/or communication for near-field energy transfer, power transfer, data transfer or combinations thereof. More specifically, the present teachings apply to wireless transmission and/or communication for near-field energy networks, power networks or data networks, including any and all combinations of such networks.

Wireless energy transfer or wireless power transmission is the transmission of electrical energy from a power source to an electrical load without interconnecting wires. For wireless transmission of energy, power or data, efficiency is a significant parameter, as the transmission signal must arrive at the receiver or receivers to make the system practical. The most common form of wireless transmission involving energy, power, or data transfer is carried out using direct induction followed by resonant magnetic induction. Other methods currently being considered include electromagnetic radiation, for example but not limited to, microwaves or lasers.

In addition, wireless energy reception or wireless power reception is the reception of electrical energy from a power source without interconnecting wires. For wireless reception of energy, power or data, efficiency is a significant parameter, as the reception of a signal must be received from a transmitter or transmitters to make the system practical. As such, the forms of wireless reception embodying energy, power or data can be carried out using direct induction, resonant magnetic induction as well as electromagnetic radiation in the form of microwaves or lasers.

Furthermore, the embodiments of the present invention are capable of wireless communication of electrical energy, electrical power and/or data without interconnecting wires. Wireless communication embodies the transmission and/or reception of electrical energy, electrical power or data either simultaneously or independently.

One aspect of the present teachings is a resonator for wireless power and/or data transfer or reception wherein resistive losses within the resonator are minimized by maximizing useful conductor cross-sectional area in a wire cross section. In one embodiment, the resonator mitigates the unwanted high frequency skin effect by introducing non-conducting dielectric layers within its wire, resulting in a structure that comprises layers of conducting material alternating with layers of non-conducting material. The structure effectively provides an increased number of surfaces each with its characteristic skin depth and all electrically, or otherwise, connected. The skin depth may range from approximately one-half of the conductor depth to about equal to the conductor depth. The conductor depth may be in the range of skin depth to twice the skin depth. However, depending on the available technology, costs, and application, the conductor depth may be as large as twenty times or more the skin depth.

The resonator includes a coil having at least one turn wherein the coil is made up of a multi-layer wire. The multi-layer wire may include a first and second conductive layer separated by a layer of insulating material. The conductive layers may have substantially the same thickness and/or depth, wherein the thickness and/or depth may be in the range of skin depth to twice the skin depth. However, depending on the available technology, costs, and application, the conductor thickness and/or depth may be as large as twenty times or more the skin depth. Each conductive layer may be electrically connected to each other using at least one method of interconnect, such as but not limited to a via, a solder, a tab, a wire, a pin, or a rivet.

One purpose of the non-conducting layer is to insulate two different conducting layers. The most basic design of the non-conducting layer would ideally be as thin as the manufacturing process practically permits, while still providing sufficient insulating properties. For example, in PCB technology, the thickness of layers is dictated by the "core thickness" and the pre-preg thickness. In another design, the thickness of the non-conducting layer is selected to modify the electrical behavior of the structure.

The resonator may have a quality factor greater than 100. Preferably, the quality factor is greater than 350. Most preferably, the quality factor is greater than 600. It will be apparent to those skilled in the art that systems requiring two resonators may either have resonators with equal and even similar quality factors. Also, it will be apparent to one skilled in the art that systems requiring two resonators may utilize resonators where one resonator has a quality factor substantially different from the other. The quality factor selection for each resonator will depend on the application, the design specification for each and the intended use of each resonator. It is understood that traditional inductively coupled systems utilize resonators with a quality factor around 30. Additionally, it will be apparent to one skilled in the art that the quality factor of a resonator may be dependent on the environment in which it is used, so, for example, a resonator that has a quality factor of 100 in air, may only have a quality factor of 50 when implanted in human or animal tissue. In any given environment, the MLMT structure described herein should outperform traditional resonators.

As a result, the reduction of losses in the wire and the significantly reduced internal resistance of the resonator could enable high efficiency, extended range, compact wireless systems that consume less energy, have longer run time and simplify operation without compromising events like overheating.

In one example, there is disclosed a structure for wireless transmission or wireless reception. The structure is designed to wirelessly transmit and/or receive electrical energy, electromagnetic energy, and/or electrical power. In addition, the structure is capable of electronic data transmission. Furthermore, the structure is capable of transmitting and/or receiving a combination of electrical energy, electromagnetic energy, electrical power and electronic data together or separately.

The structure may comprise a plurality of conductor layers, an insulator layer separating each of the conductor layers, and at least one connector connecting two or more of the conductor layers. Each of the plurality of conductor layers may have at least one turn and may further be placed in a parallel orientation. Each conductor layer may be formed from an electrically conductive material. The electrically conductive material may be comprised of copper titanium, platinum and platinum/iridium alloys, tantalum, niobium, zirconium, hafnium, nitinol, Co—Cr—Ni alloys, stainless steel, gold, a gold alloy, palladium, carbon, silver, a noble metal or a biocompatible material and any combination thereof. The conductor layer may have a cross-sectional shape, such as, but not limited to, a circular cross-section, a rectangular cross-section, a square cross-section, a triangular cross-section, or an elliptical cross-section. The connector connecting the conductor layers may be but is not limited to a via, a solder, a tab, a wire, a pin, or a rivet.

The structure may have structural shape, such as but not limited to a circular solenoidal configuration, a square solenoidal configuration, a circular spiral configuration, a square spiral configuration, a rectangular configuration, a triangular configuration, a circular spiral-solenoidal configuration, a square spiral-solenoidal configuration, and a conformal solenoid configuration. Other configurations may be used to modify the electrical properties of the structure.

An electrical resistance in the structure may be reduced when an electrical signal is induced in the resonator at a frequency. The frequency may be selected from a frequency range from about 100 kHz to about 10 GHz. Further, the frequency may be a frequency band that ranges from or is within about 100 kHz to about 10 GHz. The electrical signal may be an electrical current, an electrical voltage, a digital data signal or any combination thereof.

In another example, there is disclosed a resonator for wireless transmission or wireless reception. The resonator is designed to wirelessly transmit and/or receive electrical energy, electromagnetic energy, and electrical power. In addition, the resonator is capable of electronic data transmission or reception. Furthermore, the resonator is capable of transmitting and/or receiving a combination of electrical energy, electromagnetic energy, electrical power and electronic data together or separately.

The resonator may comprise a plurality of conductors, each conductor having a conductor length, a conductor height, a conductor depth, and a conductive surface having a skin depth. The skin depth may range from approximately one-half of the conductor depth to about equal to the conductor depth. The conductor depth may be in the range of skin depth to twice the skin depth. However, depending on the available technology, costs, and application, the conductor depth may be as large as twenty times or more the skin depth. The plurality of conductor layers may have at least one turn. Further, each of the plurality of conductor layers may or may not have substantially the same conductor length, conductor height, or conductor depth. The conductor layers may be formed from an electrically conductive material. The electrically conductive material may be comprised of copper, titanium, platinum and platinum/iridium alloys, tantalum, niobium, zirconium, hafnium, nitinol, Co—Cr—Ni alloys, stainless steel, gold, a gold alloy, palladium, carbon, silver, a noble metal or a biocompatible material and any combination thereof.

The plurality of conductors may be arranged to form a resonator body. The resonator body may have a resonator body length, a resonator body width and a resonator body depth. When an electrical signal is induced through the resonator body, the electrical signal propagates through the conducting surface of skin depth. The electrical signal may be an electrical current, an electrical voltage, a digital data signal or any combination thereof.

The plurality of conductors in the resonator may comprise a first conductor layer and a second conductor layer separated by an insulator layer wherein the first conductor layer is connected to the second conductor layer or more by at least one connector. The conductor may have a cross-sectional shape, such as but not limited to a circular cross-section, a rectangular cross-section, a square cross-section, a triangular cross-section, or an elliptical cross-section. The resonator may have a structural shape such as but not limited to a circular solenoidal, a square solenoidal configuration, a circular spiral configuration, a square spiral configuration, a rectangular configuration, a triangular configuration, a circular spiral-solenoidal configuration, a square spiral-solenoidal configuration, or a conformal solenoid configuration.

There is also disclosed a circuit for wireless transmission or wireless reception. The circuit is designed to wirelessly transmit and/or receive electrical energy, electromagnetic energy, and electrical power. In addition, the circuit is capable of electronic data transmission. Furthermore, the circuit is capable of transmitting a combination of electrical energy, electromagnetic energy, electrical power and electronic data together or separately.

Circuits at high frequencies extensively use passive elements such as inductors, capacitors, and the like. Some examples of such circuit configurations include but are not limited to band pass, high pass and low pass filters; mixer circuits (e.g., Gilbert Cell); oscillators such as Colpitts, Pierce, Hartley, and clap; and, amplifiers such as differential, push pull, feedback, and radio-frequency (RF). Specifically, inductors are used in matching and feedback in low noise amplifiers (LNAs) as a source degeneration element. Lumped inductors are also essential elements in RF circuits and monolithic microwave integrated circuits (MMICs). Lumped inductors are used in on-chip matching networks where transmission line structures may be of excessive length. Often, they are also used as RF chokes allowing bias currents to be supplied to circuits while providing broad-band high impedance at RF frequencies and above. RF MEMS switches, matching networks and varactors that are ideal for reconfigurable networks, antennas and subsystems also need high Q inductors. Note, passive circuit element and lumped element, such as lumped inductor, may be used interchangeably with passive circuit element being the broader term. The passive circuit element may be an inductor, a capacitor, a resistor or just a wire. In nearly all the above mentioned circuit examples, not meant to be limiting, it is desired that the passive components are minimally lossy.

Given circuits at high frequencies extensively use passive elements such as inductors and capacitors, an embodiment is given using but is not limited to an inductor. Specifically considering an inductor, the designs should be such that maximum Q is attained while achieving the desired inductance value. In other words, the resistive loss in the inductor needs to be minimized. Depending on the frequency of operation, available area on the substrate, the application and the technology, the inductor can be implemented as, but not limited to, a TEM/transmission line, a conductive loop, or a spiral/solenoid/combination structure of several shapes, for example, but not limited to, a circle, a rectangle, an ellipsoid, a square, or an irregular configuration. All these embodiments, not meant to be limiting, may be realized using the multi-layer structure in the present invention.

In another example, a resonator as part of a larger circuit is discussed. A resonator is a device or a system that exhibits resonance (i.e., oscillates) at specific frequency, frequencies, or frequency band(s), called the resonance frequency, frequencies, or frequency band(s). At the resonance frequency, frequencies, or frequency band(s), there is minimum impedance to oscillation. In the context of electrical circuits, there is minimum electrical impedance at the resonance frequency, frequencies, or frequency band(s). The MLMT structure of the present invention may act as a resonator under two fundamental conditions: (1) When the MLMT structure is designed to resonate at a specific frequency, frequencies, or frequency band(s), in its environment without any additional electrical components; (2) When the MLMT structure is designed to resonate at a specific frequency, frequencies, or frequency band(s), in its environment in combination with other components (for example, but not limited to, a capacitor, a capacitor bank, a capacitor and/or an inductor network). Thus, the resonator may be part of a larger circuit, and the resonance behavior may be designed to occur at a frequency, frequencies, or frequency band(s), or at a frequency, frequencies, or frequency band(s) with a certain bandwidth or certain bandwidths. Additional components (e.g., resistance) may also be added to alter the bandwidth(s).

There is also disclosed a system for wireless transmission or wireless reception. The system is designed to wirelessly transmit and/or receive electrical energy, electromagnetic energy, and electrical power. In addition, the system is capable of electronic data transmission. Furthermore, the system is capable of transmitting a combination of electrical energy, electromagnetic energy, electrical power and electronic data together or separately.

The system may comprise a first resonator comprising a plurality of first conductors, each first conductor having a first conductor length, a first conductor height, a first conductor depth, and a first conductive surface having a first skin depth. The plurality of first conductors may be arranged to form a first resonator body having a first resonator body length, a first resonator body width and a first resonator body depth. The system may also include a second resonator comprising a plurality of second conductors, each second conductor having a second conductor length, a second conductor height, a second conductor depth, and a second conductive surface having a second skin depth. The plurality of second conductors may be arranged to form a second resonator body having a second resonator body length, a second resonator body width and a second resonator body depth. The first skin depth and the second skin depth may be approximately one-half of the conductor depth to about equal to the conductor depth. The first and second conductors may have at least one turn and each of the plurality of first and second conductor layers may or may not have substantially the same conductor length, conductor height, and conductor depth. The first conductor depth and the second conductor depth may be in the range of skin depth to twice the skin depth. However, depending on the available technology, costs, and application, the first conductor depth and the second conductor depth may be as large as twenty times or more the skin depth. The first and second conductor layers may be formed from an electrically conductive material such as, but not limited to, copper, titanium, platinum and platinum/iridium alloys, tantalum, niobium, zirconium, hafnium, nitinol, Co—Cr—Ni alloys, stainless steel, gold, a gold alloy, palladium, carbon, silver, a noble metal or a biocompatible material and any combination thereof.

When an electrical signal is propagated through the first resonator body, the electrical signal propagates through the first conducting surface of skin depth and further induces an electrical signal through the second resonator body. The induced electrical signal propagates through the second conducting surface at skin depth. The electrical signal may be an electrical current, an electrical voltage, and a digital data signal, or combinations thereof.

The plurality of first conductors may comprise a first conductor layer and a second conductor layer separated by an insulator layer wherein the first conductor layer is connected to the second conductor layer or more by at least one connector. The connector connecting the conductor layers may be, but is not limited to, a via, a solder, a tab, a wire, a pin, or a rivet. The first conductor may have a first cross-sectional shape and the second conductor may have a second cross-sectional shape. The first and the second cross-sectional shapes are non-limiting and may be one of a circular cross-section, a rectangular cross-section, a square cross-section, a triangular cross-section, or an elliptical cross-section.

The first resonator may have a first structural shape and the second resonator may have a second structural shape. The first and the second structural shapes are non-limiting and may be a circular solenoidal configuration, a square solenoidal configuration, a circular spiral configuration, a square spiral configuration, a rectangular configuration, a triangular configuration, a circular spiral-solenoidal configuration, a square spiral-solenoidal configuration, or a conformal solenoid configuration.

In addition, there is disclosed a method for manufacturing a structure for wireless transmission or wireless reception. The method of manufacturing creates a structure that is capable of wirelessly transmitting and/or receiving electrical energy, electromagnetic energy, and electrical power. In addition, the resulting structure is capable of electronic data transmission or reception. Furthermore, the resulting structure is capable of transmitting and/or receiving a combination of electrical energy, electromagnetic energy, electrical power and electronic data together or separately.

The method may comprise the steps of creating a plurality of conductor layers having an insulator between each of the conductor layers and forming at least one connection between two of the plurality of conductors. The connector connecting the conductor layers may be but is not limited to a via, a solder, a tab, a wire, a pin, or a rivet. The conductor layers may be created by depositing through a mask. The step of creating a plurality of conductor layers having an insulator between each of the conductor layers may further include the steps of placing a first conductive layer on top of a second conductive layer and separating the first conductive layer from the second conductive layer with a first insulator. Further, the step of forming at least one connection between two of the plurality of conductors may include the steps of connecting at least two of the conductive layers comprising but not limited to a via, a solder, a tab, a wire, a pin, or a rivet. The conductor layers may be formed from an electrically conductive material. The electrically conductive material may be comprised of copper, titanium, platinum and platinum/iridium alloys, tantalum, niobium, zirconium, hafnium, nitinol, Co—Cr—Ni alloys, stainless steel, gold, a gold alloy, palladium, carbon, silver, a noble metal or a biocompatible material and any combination thereof.

There is also disclosed a method for operating a structure to provide wireless transmission or wireless reception. The method comprises the steps of providing a structure that is capable of wireless transmission and/or wireless reception of electrical energy, electromagnetic energy, and/or electrical power. In addition, the method provides the steps of providing a structure that is capable of electronic data transmission or reception. Furthermore, the method provides the steps of providing a structure that is capable of transmitting and/or receiving a combination of electrical energy, electromagnetic energy, electrical power and electronic data together or separately.

The method comprises the steps of providing a plurality of conductors, each conductor having a conductor length, a conductor height, a conductor depth, and a conductive surface having a skin depth. Further, the method comprises the steps of providing the skin depth to range approximately one-half of the conductor depth to about equal to the conductor depth. The conductor depth may be in the range of skin depth to twice the skin depth. However, depending on the available technology, costs, and application, the conductor depth may be as large as twenty times or more the skin depth. The plurality of conductors may be arranged to form a resonator body having a resonator body length, a resonator body width and a resonator body depth; and, inducing an electrical signal in at least one of the plurality of conductors such that the electrical signal propagates through the conducting surface of the skin depth. The electrical signal may be an electrical current, an electrical voltage, a digital data signal or any combination thereof.

The method may also include the step of providing a second plurality of conductors, each of the second conductors having a second conductor length, a second conductor height, a second conductor depth, and a second conductive surface having a second skin depth wherein the plurality of second conductors are arranged to form a second resonator body having a second resonator body length, a second resonator body width and a second resonator body depth. When an electrical signal is propagated through the resonator body, the electrical signal propagates through the conducting surface of the skin depth and further induces an electrical signal through the second resonator body, and the induced electrical signal propagates through the second conducting surface at the second skin depth.

The plurality of conductors may comprise a first conductor layer and a second conductor layer separated by an insulator layer wherein the first conductor layer is connected to the second conductor layer by at least one connector. Further, the at least one connection connecting at least two of the conductive layers comprises but is not limited to a via, a solder, a tab, a wire, a pin, or a rivet. The conductor may have a cross-sectional shape not limited to a circular cross-section, a rectangular cross-section, a square cross-section, a triangular cross-section, and an elliptical cross-section. The plurality of conductor layers may have at least one turn and each of the plurality of conductor layers may or may not have substantially the same conductor length, conductor height, and conductor depth. The conductor layer may be formed from an electrically conductive material. The electrically conductive material may be comprised of copper titanium, platinum and platinum/iridium alloys, tantalum, niobium, zirconium, hafnium, nitinol, Co—Cr—Ni alloys, stainless steel, gold, a gold alloy, palladium, carbon, silver, a noble metal or a biocompatible material or any combination thereof.

The resonator may have a structural shape not limited to a circular solenoidal configuration, a square solenoidal configuration, a circular spiral configuration, a square spiral configuration, a rectangular configuration, a triangular configuration, a circular spiral-solenoidal configuration, a square spiral-solenoidal configuration, and a conformal solenoid configuration. Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 5A illustrates an example of an antenna in a circular solenoidal configuration;

FIG. 5B illustrates an example of an antenna in a square solenoidal configuration;

FIG. 7E illustrates an example of an antenna having an elliptical cross-section;

FIG. 7F illustrates a rectangular cross-section of a multi-layer wire;

FIG. 8A illustrates a multi-layer wire having a circular cross-section;

FIG. 8B illustrates a multi-layer wire having a rectangular cross-section;

FIG. 9A shows a single turn antenna having 1 layer;

FIG. 9B shows a single turn antenna having 11 layers;

FIG. 9C shows a single turn antenna having 20 layers;

FIG. 9D shows a single turn antenna having 26 layers;

FIG. 11A is a graph illustrating the relative changes in resistance and inductance with the number of layers;

FIG. 11B is a graph illustrating the resultant quality factor at 10 MHz for the given number of layers;

FIG. 23A illustrates an equivalent circuit diagram for an MLMT structure showing a capacitor addition in series;

FIG. 23B illustrates an equivalent circuit diagram for an MLMT structure showing a capacitor addition in parallel;

FIG. 24A illustrates an equivalent circuit diagram for an MLMT structure operating as a resonator in a circuit where resonance is achieved by adding a capacitor in parallel;

FIG. 24B illustrates an equivalent circuit diagram for an MLMT structure operating as a stand alone resonator where resonance is achieved by adding a capacitor to the circuit in series;

FIG. 24C illustrates an equivalent circuit diagram for an MLMT structure operating as a stand alone resonator where resonance is achieved by adding a capacitor to the circuit in parallel;

DETAILED DESCRIPTION

Figure 1:
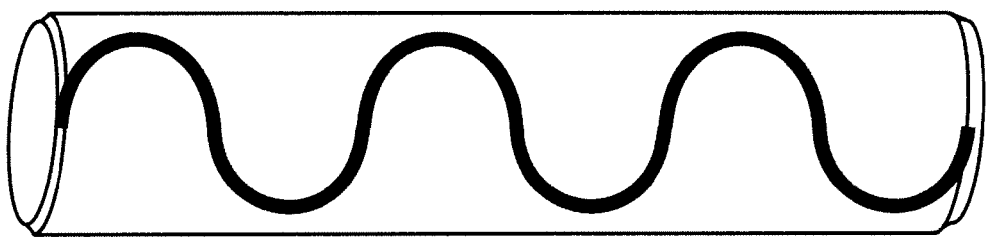
FIG. 1 illustrates an AC current distribution for a steady unidirectional current through a homogeneous conductor.

In the following description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various technologies disclosed herein generally relate to methods, systems and apparatus to design, operate and manufacture wireless transmission and/or wireless reception systems, and more specifically, to methods, systems and apparatus to design, operate and manufacture a high efficiency structure for use in near-field wireless transmission and/or reception.

Wireless transmission may embody wireless transmission of electrical energy, electromagnetic energy, and electrical power such as the embodiments. In addition, wireless transmission may embody the transmission of digital data and information. In a further embodiment, a combination of electrical energy, electromagnetic energy, electrical power, electronic data and information may be transmitted together or separately such as the embodiments discussed in energy networks. It is further contemplated that such wireless transmission could occur at the same time or over a period of time intervals. Further embodiments of wireless transmission are discussed in the energy networks, power networks, data networks and near-field power and data transfer system sections below.

Wireless reception may embody wireless reception of electrical energy, electromagnetic energy, and electrical power such as the embodiments. In addition, wireless reception may embody the reception of digital data and information. In a further embodiment, a combination of electrical energy, electromagnetic energy, electrical power, electronic data and information may be received together or received separately such as the embodiments discussed in energy networks. It is further contemplated that such wireless reception could occur at the same time or over a period of time intervals. Further embodiments of wireless reception are discussed in the energy networks, power networks, data networks and near-field power and data transfer system sections below.

Wireless communication may embody wireless transmission and reception of electrical energy, electromagnetic energy, and electrical power such as the embodiments. In addition, wireless communication may embody the transmission and reception of digital data and information. In a further embodiment, a combination of electrical energy, electromagnetic energy, electrical power, electronic data and information may be transmitted and received together or transmitted and received separately such as the embodiments discussed in energy networks. It is further contemplated that such wireless transmission and reception could occur at the same time or over a period of time intervals. Further embodiments of wireless communication are discussed in the energy networks, power networks, data networks and near-field power and data transfer system sections below.

An antenna is generally a conductor by which electromagnetic waves are sent out or received. An antenna may consist of, but is not limited to, a wire or a set of wires. A resonator is generally any device or material that resonates, including any system that resonates. A resonator may be an instrument for detecting the presence of a particular frequency by means of resonance, and may also be any circuit having this frequency characteristic. Further, a resonator may be an electrical circuit that combines capacitance and inductance in such a way that a periodic electric oscillation will reach maximum amplitude. As appreciated by those skilled in the art, antennas often act as resonators when, for example, they self resonate or when they are coupled with another reactive element such as a capacitor to achieve resonance. As such, the terms antenna and resonator are often used interchangeably herein, and are also referred to generically as a structure (e.g., multi-layer multi-turn structure).

"Skin effect" is generally the tendency for an alternating current to concentrate near the outer part or "skin" of a conductor. As illustrated in FIG. 1, for a steady unidirectional current through a homogeneous conductor, the current distribution is generally uniform over the cross section; that is, the current density is the same at all points in the cross section.

Figure 2:
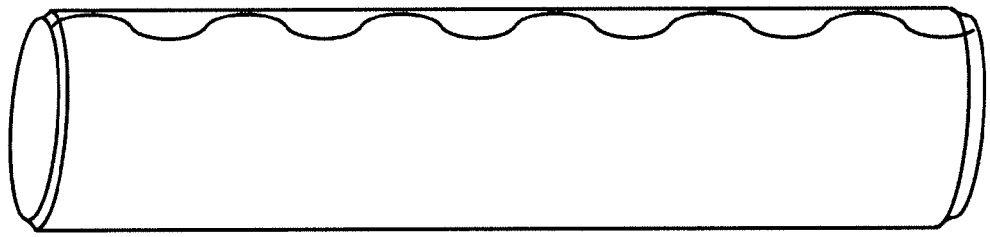
FIG. 2 illustrates an AC current distribution at increased frequency due to skin effect.

With an alternating current, the current is displaced more and more to the surface as the frequency increases. This current does not effectively utilize the full cross section of the conductor. The conductor's effective cross section is therefore reduced so the resistance and energy dissipation are increased compared with the values for a uniformly distributed current. In other words, as illustrated in FIG. 2, due to the skin effect, the current density is maximum near the surface (also called the "skin") of the conductor and decays exponentially to the center of the cross-section.

The effective resistance of a wire rises significantly with frequency. In a preferred embodiment, this frequency may range from about 100 kHz to about 3 MHz and more preferably from about 3 MHz to about 10 GHz. In an embodiment necessitating large antenna construction operating at 120 KHz, it may even be beneficial to create a MLMT structure using large gauge wires/materials to achieve efficient performance.

Figure 3:
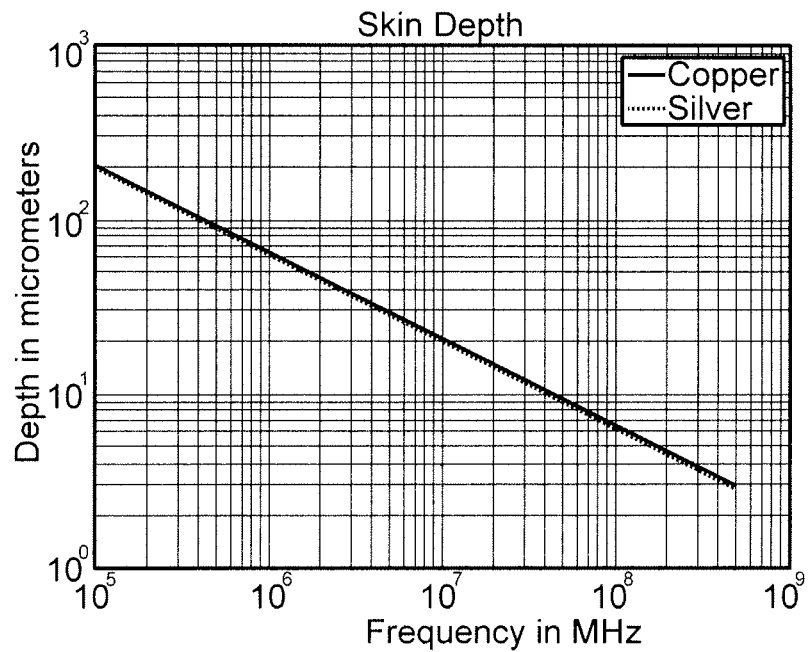
FIG. 3 is a graph of skin depth vs. frequency.

For a copper wire of 1-mm (0.04-in.) diameter for example, the resistance at a frequency of 1 MHz is almost four times the dc value. "Skin depth" or "penetration depth" $\delta$ is frequently used in assessing the results of skin effect. It is generally accepted that the depth below the conductor surface at which the current density has decreased to about 1/e (approximately 37%) of its value at the surface. The term "skin depth" is therefore described as the depth within the cross-section where the current density has dropped to about 37% of the maximum. This concept applies to plane solids, but can be extended to other shapes provided the radius of curvature of the conductor surface is appreciably greater than $\delta$. For example, at a frequency of 60 Hz the penetration depth in copper is 8.5 mm (0.33 in.); at 10 GHz it is only $6.6 \times 1^{0-7}$ m. The skin depth is a strong function of frequency and decreases with increasing frequency. This phenomenon is displayed in the graph shown in FIG. 3.

The fundamental concept of the multi-layer wire is to maximize the available current density over the full wire cross-section thereby reducing the wire's intrinsic resistance. By using a conductive layer whose thickness is about twice the skin depth, it is ensured that the current density at all points in the wire is greater than or equal to ~37% of the maximum possible current density (at surface). By using other layer thicknesses, a different base current density will be obtained. For example, by using a layer thickness of about 4 times the skin depth, it will be ensured that current density is greater than or equal to ~14% of the maximum possible current density (at surface). Similarly, for conductor depth approximately 6 times the skin depth, the current density is greater than or equal to 5%.

While it is important to keep a high current density in the conductive layers, at the same time, it is essential that the unused cross-sectional area, i.e., the insulating layer, be as small as possible overall. Using the above theory, an ideal proposed configuration for a multilayer wire includes conductive layers with thickness/depth about twice the skin depth, and an insulating layer, as thin as technologically possible. To those skilled in the art it will be understood that MLMT structures may result in embodiments wherein the skin depth, which is the conductive area active in wireless communication, ranges from approximately one-half of the conductor depth to about equal to the conductor depth. On the other hand, given limitations imposed by some fabrication methods, designing MLMT structures may also result in embodiments wherein the conductor depth, which is the area capable of conducting a signal but not necessarily fully utilized as operating frequencies increase, ranges from skin depth to about twice the skin depth.

Wave-guide and resonant cavity internal surfaces for use at microwave frequencies are therefore frequently plated with a high-conductivity material, such as silver, to reduce the energy losses since nearly all the current is concentrated at the surface. Provided the plating material is thick compared to $\delta$, the conductor is as good as a solid conductor of the coating material. "Quality factor" is generally accepted as an index (figure of measure) that measures the efficiency of an apparatus like an antenna, a circuit, or a resonator. Via is defined herein as an electrically conductive connection from one layer to another.

A Litz wire is generally a wire constructed of individual film insulated wires bunched or braided together in a uniform pattern of twists and length of lay.

Figure 4:
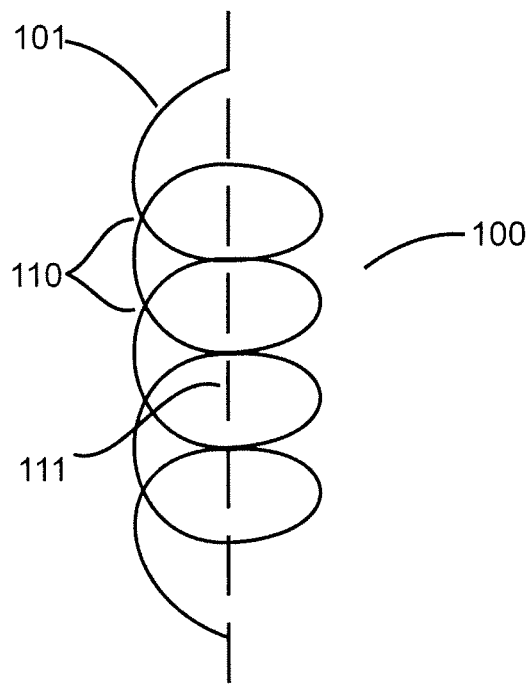
FIG. 4 illustrates a high-level diagram of a structure for wireless power transfer.

Reference now is made in detail to the examples illustrated in the accompanying drawings and discussed below. FIG. 4 illustrates a high-level diagram of a resonator for wireless power and/or data transfer, such as an antenna. The resonator includes a coil 100 and a multi-layer wire 101. The shape of the coil 100 may be circular, rectangular, triangular, some other polygon, or conformal to fit within a constrained volume. FIG. 4 illustrates one exemplary configuration of a coil in the form of a circular shaped coil 100. The configuration of the coil 100 may be solenoidal, spiral, or spiral-solenoid. A solenoid coil follows a helical curve that may have multiple turns where each turn has the same radius. A spiral coil configuration may have a number of turns with a progressively increasing or decreasing radius. A spiral-solenoidal coil configuration is a combination of a spiral and solenoidal configuration. Other configurations known to those of ordinary skill may also be utilized to form the coil.

Figure 5C:
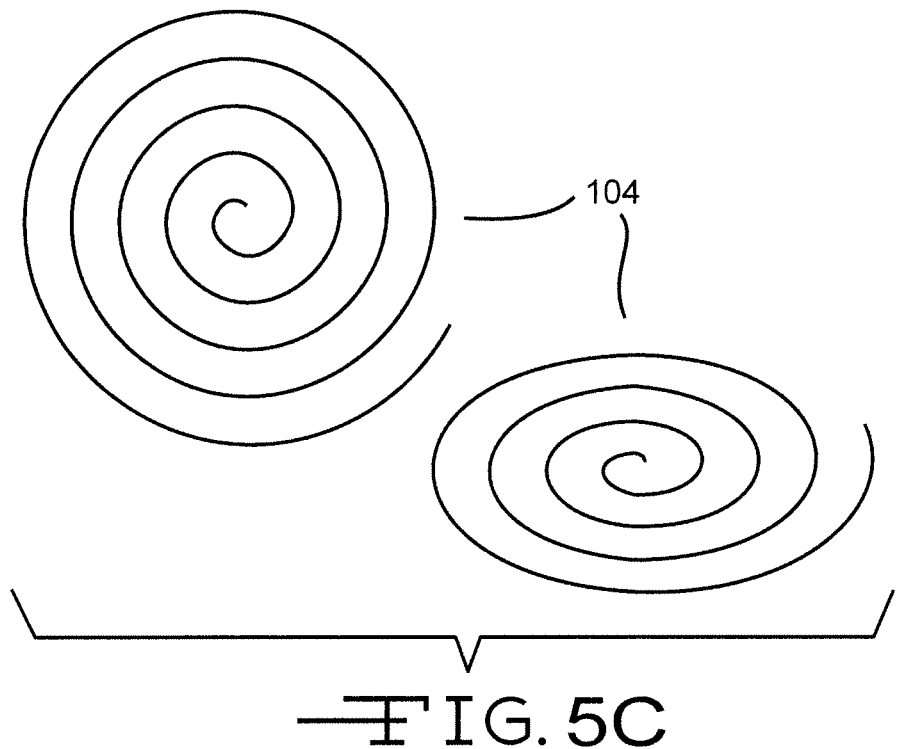
FIG. 5C illustrates an example of an antenna in a circular spiral configuration.
Figure 5D:
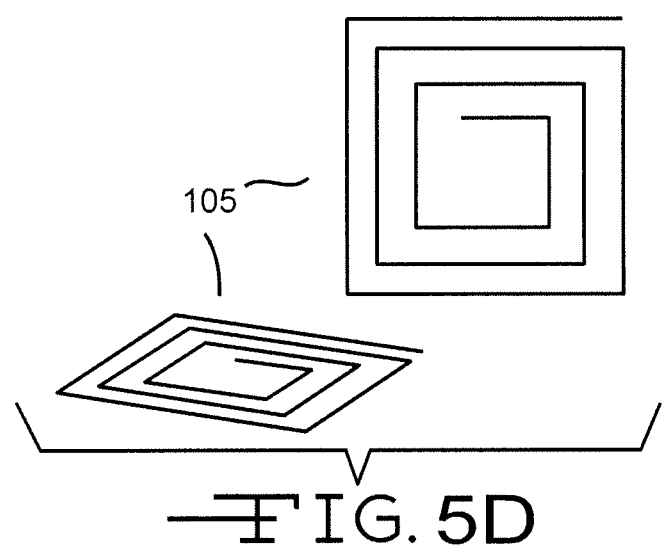
FIG. 5D illustrates an example of an antenna in a square spiral configuration.
Figure 5E:
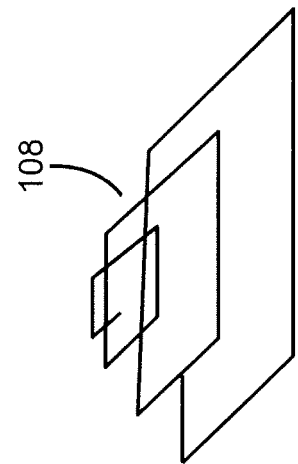
FIG. 5E illustrates an example of an antenna in a multi-layer square spiral configuration.

FIGS. 5A-5H illustrate examples of different antenna configurations that may be utilized. FIG. 5A illustrates an example of an antenna in a circular solenoidal configuration 102. FIG. 5B illustrates an example of an antenna in a square solenoidal configuration 103. FIG. 5C illustrates an example of an antenna in a circular spiral configuration 104. FIG. 5D illustrates an example of an antenna in a square spiral configuration 105. It is understood that other spiral configurations, such as rectangular or triangular shape may also be utilized. FIG. 5E illustrates an example of an antenna in a multi-layer square spiral configuration 106. It should be noted that although only two layers are illustrated in FIG. 5E, it is understood that any number of layers may be used. As will be described below, when multiple layers are used, the multiple layers may be connected using but not limited to vias, solder, tabs, wires, pins, or rivets. In one embodiment, the plurality of conductor layers less than or equal to the total number of layers, may be connected electrically in parallel. Furthermore, in another embodiment, the plurality of conductor layers connected electrically in parallel may be connected electrically in series with one or more of a plurality of conductor layers connected electrically in parallel. These connectors serve at least the following two purposes: (1) the connectors connect the layers of wire for the multi-layer wire; and (2) the connectors connect one turn of the multi-layer wire to a second turn of the multi-layer wire. For example, a two-turn antenna then, there would be at least one via from the first turn to the second turn. Other purposes may also be served by the connectors.

For each antenna, there exists an optimum number of connectors and an optimum location for each connector. Since there is no closed-form analytical solution for these, the optimal locations may best be obtained through iterative modeling. However, basic guidelines for optimizing are given herewithin:

It is preferred that there be at least 2 connectors connecting all of the layers that form a single conductor. These two connectors will ideally be at the two ends of the multilayer wire (the input and the output of the multilayer wire)

It is preferred the total number of connectors should be chosen commensurate with the needs of a particular application. More than the optimum number of connectors will increase current paths which can lead to increased capacitance, increased resistance, reduced quality factor and higher bandwidth. It should also be noted that parasitic effects can become more pronounced when the overall length (height, depth) of the connector is greater than the optimum at a specific operating frequency. The length of the connector in essence is the height of the connector, and this should be kept smaller than about the (effective wavelength)/20, though keeping it within wavelength/10 could also lead to a workable embodiment, depending on the application. The reason for these restrictions is that the increased connector lengths will introduce significant phase differences between the different layers of the multilayer wire being used. These phase differences between the different layers will introduce unwanted capacitive effects, which will effectively lower self-resonance frequencies and increase losses. It should be mentioned that, for embodiments in which no additional components (for e.g. capacitors) are utilized and the structure is being used as a self-resonant resonator, connectors such as but not limited to vias with depth higher than (effective wavelength)/10 might be incorporated in the design of the antenna.

Vias can be of the form commonly used in printed circuit board (PCB) technologies (for example, through-hole, buried, blind) or those utilized in semiconductor or MEMS technology. Alternatively, the via can be, but is not limited to, any conductive material that is laser-welded, welded, printed, soldered, brazed, sputtered deposited, wire-bonded and the like in order to electrically connect at least any two layers and/or all layers.

Figure 5F:
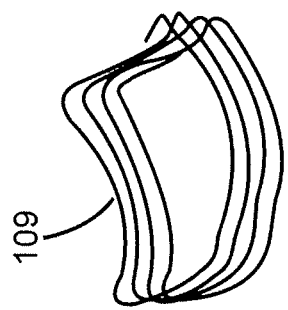
FIG. 5F illustrates an example of an antenna in a circular spiral-solenoidal configuration.
Figure 5G:
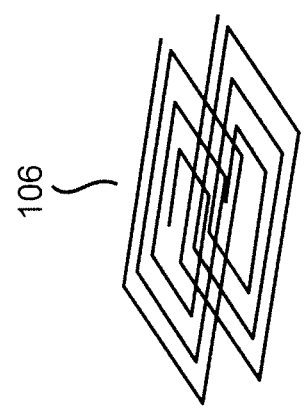
FIG. 5G illustrates an example of an antenna in a square spiral-solenoidal configuration.
Figure 5H:
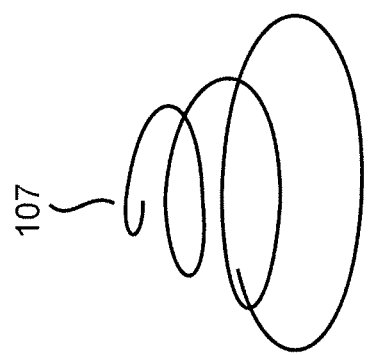
FIG. 5H illustrates an example of an antenna in a conformal solenoid configuration.

FIG. 5F illustrates an example of an antenna in a circular spiral-solenoidal configuration 107. FIG. 5G illustrates an example of an antenna in a square spiral-solenoidal configuration 108. FIG. 5H illustrates an example of an antenna in a conformal solenoid configuration 109. The antenna in a conformal configuration may take the form of but is not limited to a circular or rectangular solenoid or a circular or rectangular spiral. Any of the antenna configurations shown in FIGS. 5A-5H may be used with the present system.

Figure 6A:
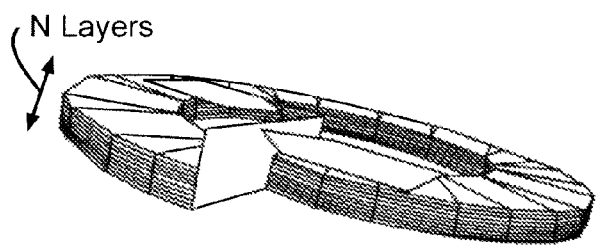
FIG. 6A illustrates an example of a single turn circular coil having N layers.
Figure 6B:
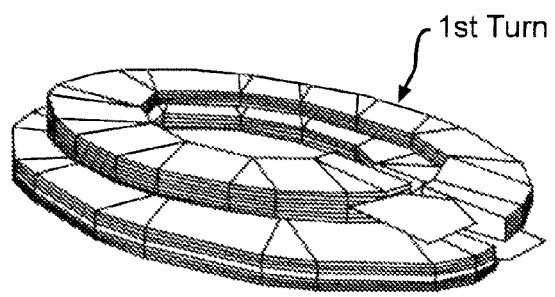
FIG. 6B illustrates an example of a double turn circular spiral-solenoidal coil of N layers.

The coil 100 of FIG. 4 may have a plurality of turns 110. A turn may be but is not limited to a bend, fold or an arc in the wire until the wire completes a revolution around the central axis point of the coil 111. A turn may be in the same or similar shape of the coil configuration, such as, for example, but not limited to a circle, a rectangle, a triangle, some other polygonal shape, or conformal to fit within a constrained volume. FIG. 6A illustrates a single turn circular coil having N layers, where "N" is a number equal to or greater than one. FIG. 6B illustrates a double turn circular solenoidal coil of N layers.

In general, for any inductive antenna, the inductance increases as $T^x$, while the resistance increases as $T^y$, where T is the number of turns. In ideal conductors, x and y are 2 and 1 respectively. There are other factors which affect the inductance and resistance (hence the quality factor) which calls for x and y to be less than 2 and 1 respectively. Referring to FIG. 13, three performance examples are given. The graph compares a 32 Layer-2 Turn antenna with a 32 Layer-1 Turn antenna and a 64 Layer-1 Turn antenna. The inductance and resistance for the 32 Layer-2 Turn antenna increase between 3-3.5 times and 1.7-3 times, respectively; over the 32 Layer-1 Turn antenna in the frequency range 1 MHz-200 MHz. This increase is very near expected values from simplistic analytical relations wherein resistance is approximately T; and inductance is approximately $T^2$.

Figure 7A:
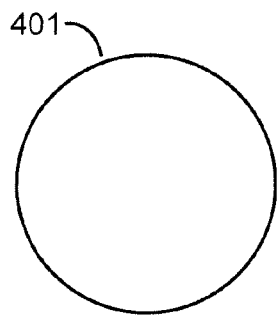
FIG. 7A illustrates an example of an antenna having a circular cross-section.
Figure 7B:
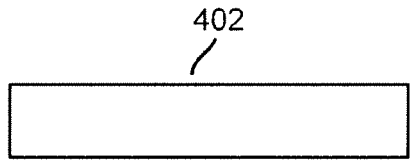
FIG. 7B illustrates an example of an antenna having a rectangular cross-section.
Figure 7C:
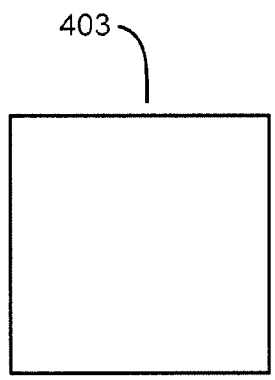
FIG. 7C illustrates an example of an antenna having a square cross-section.
Figure 7D:
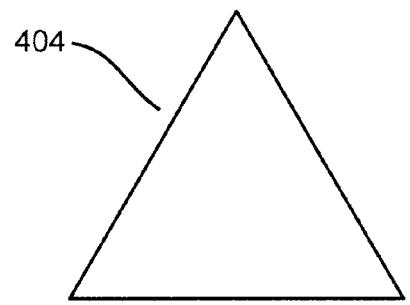
FIG. 7D illustrates an example of an antenna having a triangular cross-section.

The multi-layer wire 101 in FIG. 4 may have but is not limited to a circular, rectangular, square, or triangular cross-sectional shape. In addition, other shapes known to those of ordinary skill may also be utilized. FIGS. 7A-7E illustrate examples of cross-sections of wires that may be used in the design of an antenna. FIG. 7A illustrates an example of an antenna having a circular cross-section 401. FIG. 7B illustrates an example of an antenna having a rectangular cross-section 402. FIG. 7C illustrates an example of an antenna having a square cross-section 403. FIG. 7D illustrates an example of an antenna having a triangular cross-section 404. FIG. 7E illustrates an example of an antenna having an elliptical cross-section 405. FIG. 7F illustrates a rectangular cross-section of a multi-layer wire having a first conductive layer 410 and a second conductive layer 420. In addition to the embodiments discussed above, the multi-layer wire 101 may be comprised of a rigid wire structure, a fixed flexible wire structure or a combination thereof.

An insulating material 430 separates the first layer 410 from the second layer 420. The first layer 410 and second layer 420 are connected with vias 440 which traverse the insulating material 430. The conductive layers 410, 420 may be layers of conductive tape/ribbon/sheet/leaf or deposited metal having a metal thickness and metal strip width. The metal thickness of the first layer 410 is identified by line A-A and the metal strip width of the first layer 410 is identified by line B-B. In one example, the metal thickness of a layer may be approximately twice the skin depth. The skin depth may range from approximately one-half of the conductor depth to about equal to the conductor depth Each layer in a turn will have substantially the same metal thickness and metal strip width.

The thickness of the insulating material may be sufficient to meet the needs of the application or equal to the minimum thickness possible by the available fabrication technology. Additionally, the overall structure feasibility depends on the frequency of operation (as shown in the graph of FIG. 1), associated costs and fabrication technology utilized. Generally in PCB technology, the thickness of layers is dictated by the "core thickness" and the pre-preg thickness. In other designs, the thickness of the non-conducting layer is selected to modify the electrical behavior of a structure.

Figures 18, 19:
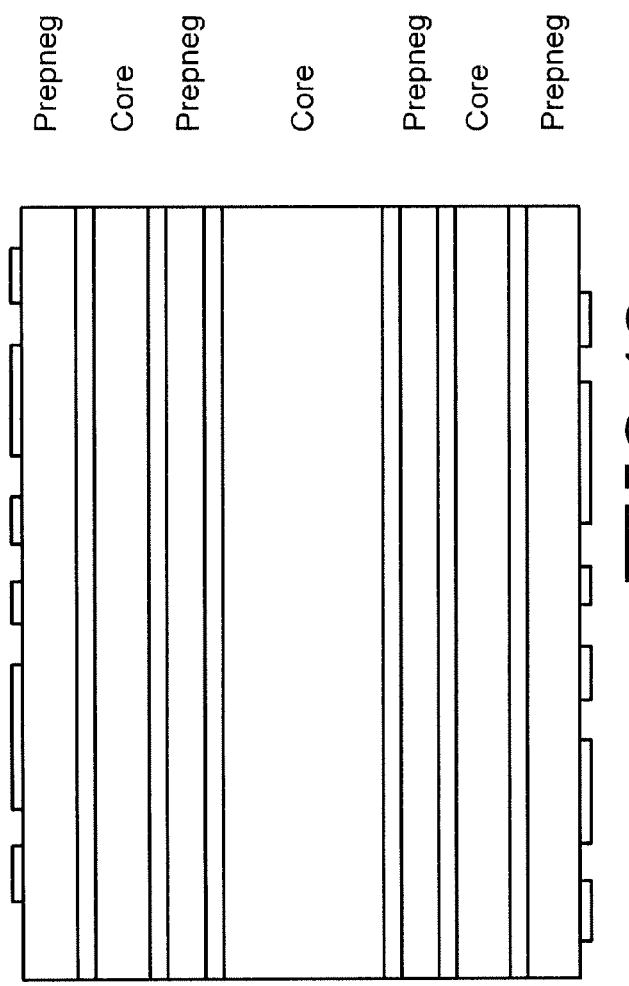
FIG. 18 illustrates a typical PCB stackup.
FIG. 19 is a table of fabrication stack up for a 6-layer PCB board as obtained from an established PCB manufacturer.

Typical PCB stackup comprises alternating layers of the core and the pre-preg. The core generally comprises a thin piece of dielectric with copper foil bonded on both sides. The core dielectric is generally cured fiberglass-epoxy resin. The pre-preg is generally uncured fiberglass-epoxy resin. The pre-preg will cure (i.e., harden) when heated and pressed. The outermost layers are generally pre-preg with copper foil bonded to the outside (surface foils). Stackup is generally symmetric about the center of the board in the vertical axis to avoid mechanical stress in the board under thermal cycling as shown in FIG. 18.

One embodiment wherein the conductor and insulating layer thicknesses are equal to the minimum thickness possible by the available fabrication technology is given for an application at 13.56 MHz. At 13.56 MHz, the skin depth is about 17.8 micrometers. Ideally, the conductor depth should be about 35.6 micrometers and the insulation thickness should be as small as possible. As shown in FIG. 19, however, in actuality, using a PCB fabrication method with standard, established, low cost techniques, the fabrication stack up obtained for a 6-layer PCB board is about 71 micrometers which is nearly 4 times the skin depth. Further, the insulating layer is more than 3 times the conductive layer. Advanced PCB techniques, which come at a significantly higher cost, may allow a lower conductor and insulation depth. For example, PCB techniques currently in the research stage, could allow the conductive material like copper as low as 5 micrometers and the insulating dielectric about 39 micrometers. Other techniques, such as semiconductor fabrication and MEMS fabrication techniques could allow much thinner layer thickness leading to performance that is nearer to ideal. If semiconductor or MEMS fabrication is used, the thicknesses of both the conducting layers and the insulating layers may be as thin as a few 100 nanometers or even thinner. In a preferred embodiment, the dielectric layer thickness is less than 200 micrometers and as perfectly insulating as possible, and with a permittivity lower than 10.

Similarly, the dielectric layer could be made from several materials, and can be of various configurations. For example, some applications may require extremely low parasitic capacitance. In such cases, a non-conducting dielectric with the lowest possible permittivity is preferred. Additionally, it may be desired to increase the insulating layer thickness to minimize the parasitic effects. Another example would be for applications that might require ferrite materials to increase inductance and/or increase magnetic shielding. In such cases, the dielectric layers might be replaced by a ferrite film/block or similar propertied configuration/material.

It will be apparent to one skilled in the art, therefore, that the insulating material will be of a thickness such that the thickness is within the practical capabilities of the manufacturing technology used to manufacture that resonator and compatible with the efficiency needs of the application for which the resonator is intended.

The material of the conductive layers may be copper or gold, however, other materials are possible. To enhance conductivity, copper or gold with a layer of deposited silver may also be used. In the case where the antenna is implanted and may be exposed to body fluids, then the typically known biocompatible materials should be utilized, including additions for enhancing conductivity. These may include, but are not limited to, conductive material taken from the group of titanium, platinum and platinum/iridium alloys, tantalum, niobium, zirconium, hafnium, nitinol, Co—Cr—Ni alloys such as MP35N, Havar®, Elgiloy®, stainless steel, gold and its various alloys, palladium, carbon, or any other noble metal. Depending on the application, the insulating material may be (i) air, (ii) a dielectric with a low permittivity (such as, for example, Styrofoam, silicon dioxide, or any suitable biocompatible ceramic), (iii) a non-conductive dielectric with a high permittivity, (iv) a ferrite material, or (v) a combination of the materials listed above. The choice of material or combination of materials may result from factors such as the fabrication process, cost and technical requirements. For example, if a high capacitive effect is required to affect a lower self-resonance frequency of an antenna, a high permittivity dielectric might be preferred, or, a combination of materials including a ferrite film or ferrite block might be preferred to increase the self-inductance of the antenna. In addition, the use of a ferrite core may be used to provide increased performance.

FIG. 8A-FIG. 8B illustrate examples of different multi-layer wire cross-sectional configurations. FIG. 8A illustrates a multi-layer wire having a circular cross-section 510. FIG. 8B illustrates a multi-layer wire having a rectangular cross-section 520. In FIG. 8B, the via 530 that connects the conductive layers 540 is positioned at the port or input 550, which is the beginning of the wire. Depending on the specific application, the positioning of the vias 530 that connect the conductive layers may impact the performance of the antenna. For example, insufficient vias may lead to phase differences between the different layers. Conversely, an abundance of vias may lead to additional cyclical current paths that may increase the resistive loss. The vias may be located at the beginning of the wire (e.g., port, input, etc), or at one or more locations along the wire. Additionally, the vias between one set of two or more conductive layers may be at a different location than another set of two or more conductive layers. It is understood that several variations may be possible depending on the application and the system design. The via can be made using techniques standard to the technology being utilized for the fabrication of the multi-layer multi-turn structure. In other cases, the vias can be implemented using soldering techniques, such as, by connecting the several layers at via locations using electric solder, welded tabs, laser weld tacking, or other commonly known electrical connecting techniques.

As will be described herein, the antenna is preferably designed with a high quality factor (QF) to achieve efficient transfer of power that reduces intrinsic resistive losses of the antenna at high frequencies. The quality factor is the ratio of energy stored by a device to the energy lost by the device. Thus, the QF of an antenna is the rate of energy loss relative to the stored energy of the antenna. A source device carrying a time-varying current, such as an antenna, possesses energy which may be divided into three components: 1) resistive energy ($W_{res}$), 2) radiative energy ($W_{rad}$), and 3) reactive energy ($W_{rea}$). In the case of antennas, energy stored is reactive energy and energy lost is resistive and radiative energies, wherein the antenna quality factor is represented by the equation $Q=W_{rea}/(W_{res}+W_{rad})$.

In near field communications, radiative and resistive energies are released by the device, in this case the antenna, to the surrounding environment. When energy must be transferred between devices having limited power stores, e.g., battery powered devices having size constraints, excessive power loss may significantly reduce the devices' performance effectiveness. As such, near-field communication devices are designed to minimize both resistive and radiative energies while maximizing reactive energy. In other words, near-field communications benefit from maximizing Q.

By example, the efficiency of energy and/or data transfer between devices in an inductively coupled system is based on the quality factor of the antenna in the transmitter (Q1), the quality factor of the antenna in the receiver (Q2), and the coupling coefficient between the two antennas ($\kappa$). The efficiency of the energy transfer varies according to the following relationship: eff$\propto \kappa^2 \cdot Q_1 Q_2$. A higher quality factor indicates a lower rate of energy loss relative to the stored energy of the antenna. Conversely, a lower quality factor indicates a higher rate of energy loss relative to the stored energy of the antenna. The coupling coefficient (K) expresses the degree of coupling that exists between two antennas.

Further, by example, the quality factor of an inductive antenna varies according to the following relationship:

$$Q = \frac{2\pi f L}{R}$$

where f is the frequency of operation, L is the inductance, and R is the total resistance (ohmic+radiative). As QF is inversely proportional to the resistance, a higher resistance translates into a lower quality factor.

A higher quality factor may be achieved using multiple layers in a multi-layer wire for a single turn of coil. Increasing the number of turns in a coil may also be used to increase the quality factor of the structure. For a design at a constant frequency, there may be an optimum number of layers to reach a maximum quality factor. Once this maxima is reached, the quality factor may decrease as more layers are added. The design variables that may be used for the multi-layer multi-turn structure include:

a. Metal strip width, $w_n$ (e.g. $w_1$: width of the 1$^{st}$ conductive layer, $w_k$: width of the k$^{th}$ conductive layer). Also referred to as metal width or strip width
b. Number of conductive layers per turn, $N_n$ (e.g. number of layers in 1$^{st}$ turn, $N_1$)
c. Thickness of each conductive layer, $d_n$ (e.g. thickness of 1$^{st}$ layer, $d_k$: thickness of k$^{th}$ layer)
d. Thickness of insulation, $di_n$ (e.g.: thickness of insulation under 1$^{st}$ layer, $di_k$: thickness of insulation under k$^{th}$ layer)
e. Number of turns, T
f. Number of vias connecting the different conductive layers in each turn
g. Location of vias connecting the different conductive layers in each turn
h. Shape (circular, rectangular, some polygon; depends on the application; for e.g. could be conformal to fit just outside or just inside some device or component)
i. Configuration: solenoidal, spiral, spiral-solenoidal, etc)
j. Dimensions (length, width, inner radius, outer radius, diagonal, etc.)

Below, exemplary multi-layer multi-turn designs based on the above parameters will be described.

In one example, the antenna may be a single turn circular coil having multi-layer wire, as illustrated in FIGS. 9A-9D. The single turn coil includes a single turn and may include a metal strip width of approximately 1.75 mm, a metal thickness of approximately 0.03 mm, an insulating layer of approximately 0.015 mm, and an outer radius of approximately 5 mm. The wire may have between 5 and 60 layers, such as 5, 11, 20, 26, 41, or 60 layers. For example, FIG. 9A shows a single turn antenna having 1 layer, FIG. 9B shows a single turn antenna having 11 layers, FIG. 9C shows a single turn antenna having 20 layers, and FIG. 9D shows a single turn antenna having 26 layers. Although specific examples are shown in FIGS. 9A-9D, it is understood that the wire may have less than 5 or more than 60 layers in order to achieve a high quality factor. The corresponding coil thickness for the range of 5 to 60 layers may be between approximately 0.2 mm to 3 mm, such as for example, 0.2, 0.5, 1, 1.25, 2.05, or 3 mm, respectively. As mentioned above, it is understood that by varying the number of layers in the wire, the number of turns, the metal thickness, and the metal strip width, a higher quality factor may be obtained. For example, for a 1 layer single turn coil having a metal thickness of 0.03 mm and a metal strip width of 1.75 mm, the quality factor at 10 MHz is approximately 80. Increasing the number of layers from 1 to 11 and keeping a metal thickness of 0.03 mm and a metal strip width of 1.75 mm, the quality factor is increased to approximately 210. Generally, an increase in the number of layers per turn results in an increase in quality factor until maxima is reached, after which the quality factor starts to decrease. This decrease may occur when the total height of the antenna becomes comparable to its radius. With electrical components, the degradation starts due to greatly increased parasitic effects due to the multiple layers (e.g. capacitance and proximity effects). In the present example, increasing the layers to 20, 26, 41 and 60 results in quality factors of approximately 212, 220, 218 and 188, respectively.

To demonstrate benefits of the present teachings vis-à-vis the prior art solutions, models of the present teachings were developed to compare with known coils. The prior art models were assumed to be made using solid wire. For a circular coil with radius r; Wire radius, $\alpha$; turns, N; inductance (L) and resistance ($R_{ohmic}$ and $R_{radiation}$) as given by the following equations:

$$L = \mu_0 N^2 r \ln\left[\left(\frac{8r}{a}\right) - 2\right]$$

$$R_{ohmic} = \sqrt{\frac{\mu_0 \rho \omega}{2}} \frac{Nr}{a}$$

$$R_{radiation} = \frac{\pi}{6} \eta_0 N^2 \left(\frac{\omega r}{c}\right)^4$$

Two antenna configurations were considered, the specifics of which are provided in the Table 1 and Table 2 below. The results indicate that the present teachings allow for significantly higher QF's than the solid wire. The performance improvement shown herein applies when other known methods of construction are utilized.

TABLE 1

Antenna Configuration-1

| Using above formula | IE3D (numerical) | Inductance | | Resistance | | Quality Factor | |
|---|---|---|---|---|---|---|---|
| | | $L_{formula}$ | $L_{numerical}$ | $R_{formula}$ | $R_{numerical}$ | $Q_{formula}$ | $Q_{numerical}$ |
| 1 turn<br>R = 1 cms<br>A (wire radius) = 1 mm<br>Wire area ~3.14 mm$^2$<br>f = 380 MHz | 1-turn<br>R = 1 cms<br>Strip width ~1 mm<br>Layer thick. ~0.01 mm<br>Total thick. ~2.5 mm<br>Total wire area ~2.5 mm$^2$<br>MLMT design | 30 nH | 28.7 nH | 0.0583 | 0.0337 | 1225 | 2034 |
| 1 turn<br>R = 1 cms<br>A (wire radius) = 1 mm<br>Wire area ~3.14 mm$^2$<br>f = 380 MHz | 1-turn<br>R = 0.5 cms<br>Strip width ~1 mm<br>Layer thick. ~0.01 mm<br>Total thick. ~2 mm<br>Total wire area ~2 mm$^2$<br>MLMT design | 30 nH | 9 nH | 0.0583 | 0.0083 | 1225 | 2671 |

TABLE 2

Antenna Configuration-2

| Using above formula | IE3D (numerical) | Inductance | | Resistance | | Quality Factor | |
|---|---|---|---|---|---|---|---|
| | | $L_{formula}$ | $L_{numerical}$ | $R_{formula}$ | $R_{numerical}$ | $Q_{formula}$ | $Q_{numerical}$ |
| 1 turn<br>R = 15 cms<br>(wire radius) = 2 mm<br>Wire area ~12.5 mm$^2$<br>f = 17 MHz | 1 turn<br>R = 15 cms<br>Strip width ~2 mm<br>Layer thick ~0.03 mm<br>Total Thick ~1 mm<br>Total wire area ~2 mm$^2$<br>MLMT design | 830 nH | 1.16 μH | 0.0815 | 0.0498 | 1161 | 2489 |
| 1 turn<br>R = 30 cms<br>(wire radius) = 2 mm<br>Wire area ~12.5 mm$^2$<br>f = 17 MHz | 1 turn<br>R = 30 cms<br>Strip width ~3 mm<br>Layer thick ~0.03 mm<br>Total Thick ~1 mm<br>Total wire area ~3 mm$^2$<br>MLMT design | 1.92 μH | 2.48 μH | 0.1854 | <0.08 | 1105 | >2500 |

Figure 10:
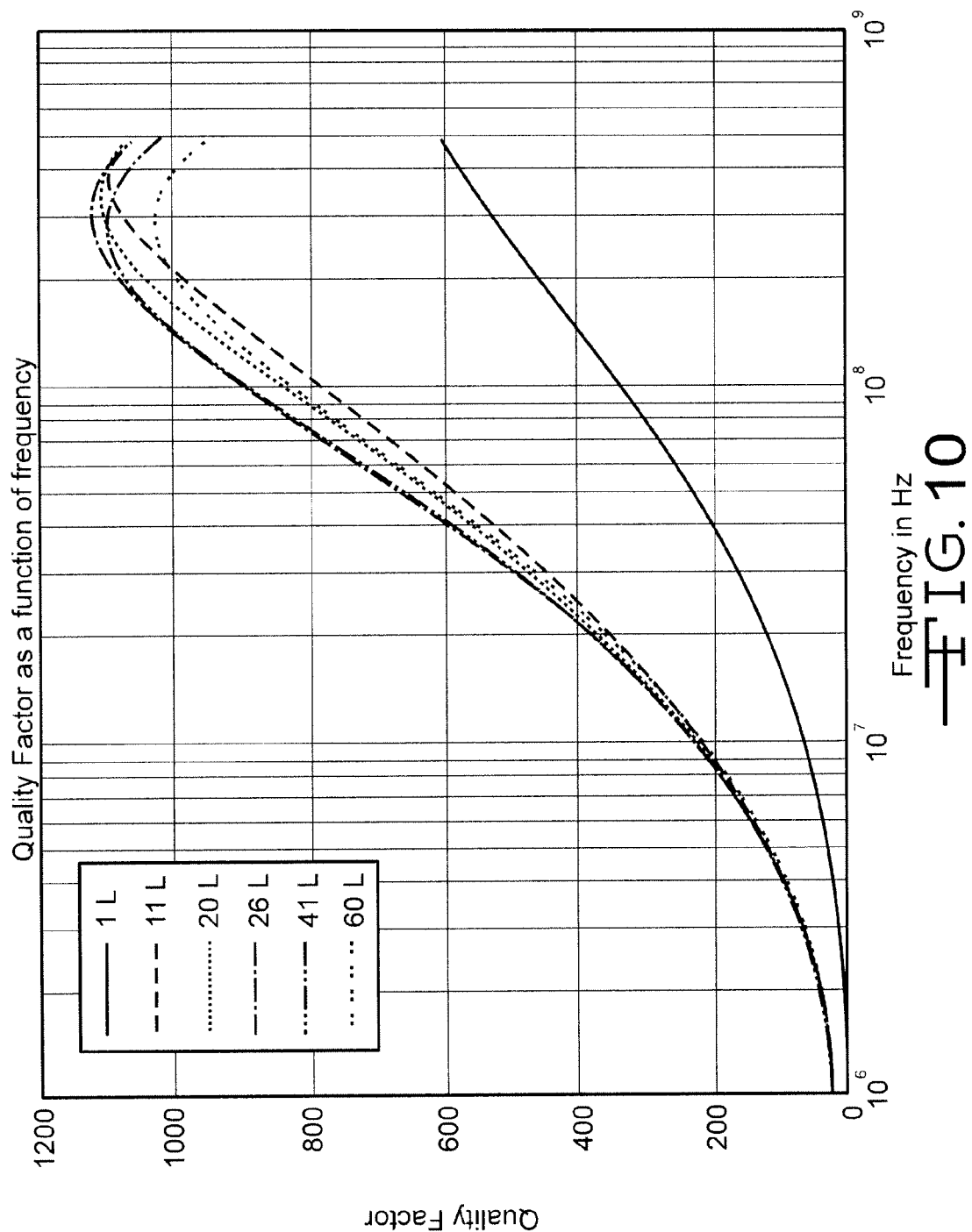
FIG. 10 is a graph illustrating the value of the quality factor as a function of frequency.

It is also understood that the metal strip width may be increased to achieve a higher quality factor. FIG. 10 provides a graph of the value of the quality factor as a function of frequency. FIG. 11A is a graph illustrating the relative changes in resistance and inductance with the number of layers. FIG. 11B illustrates the resultant quality factor at 10 MHz. It should be noted that with regard to FIGS. 11A-B, the data points on the graph correspond as data point 1 is for 1 layer, data point 2 is for 11 layers, data point 3 is for 20 layers, data point 4 is for 26 layers, data point 5 is for 41 layers, and data point 6 is for 60 layers. To ensure signal flow through all layers of the structure, it is preferable that at least two vias be included for any multi-layer wire and/or structure. These two vias are preferably located at the ports of the wire/structure. As can be seen from FIGS. 10 and 11A-B, optimal performance for 10 MHz is achieved for an antenna configuration having 26 layers and 1 turn. For this antenna configuration, the peak quality factor is obtained around 35 MHz and is approximately 1100.

In another example, the antenna may be a single turn circular coil of multi-layer wire and may have a metal strip width of approximately 1 mm, a metal thickness of approximately 0.01 mm, an insulating layer of approximately 0.005 mm, and an outer radius of approximately 5 mm. The wire may have between 16 and 128 layers, such as 16, 32, 64, or 128 layers. However it is understood that the wire may have less than 16 or more than 128 layers in order to achieve a high quality factor. The corresponding coil thickness for the range of 16 to 128 layers may be between approximately 0.25 mm to 2 mm, such as for example, 0.25, 0.5, 1, or 2 mm, respectively. In this example, the quality factor improves with increasing the number of layers, with larger quality factors achieved at higher frequencies. For example, at a frequency of 10 MHz, the quality factor for 16, 32, 64 and 128 layers is approximately 127, 135, 140 and 185, respectively. The peak quality factor increases to nearly 2900 at approximately 450 MHz under these design parameters. The relative resistance may be lowest around the frequency at which the conductor thickness is about twice the skin depth. In this example, that frequency is 160 MHz.

Figure 12A:
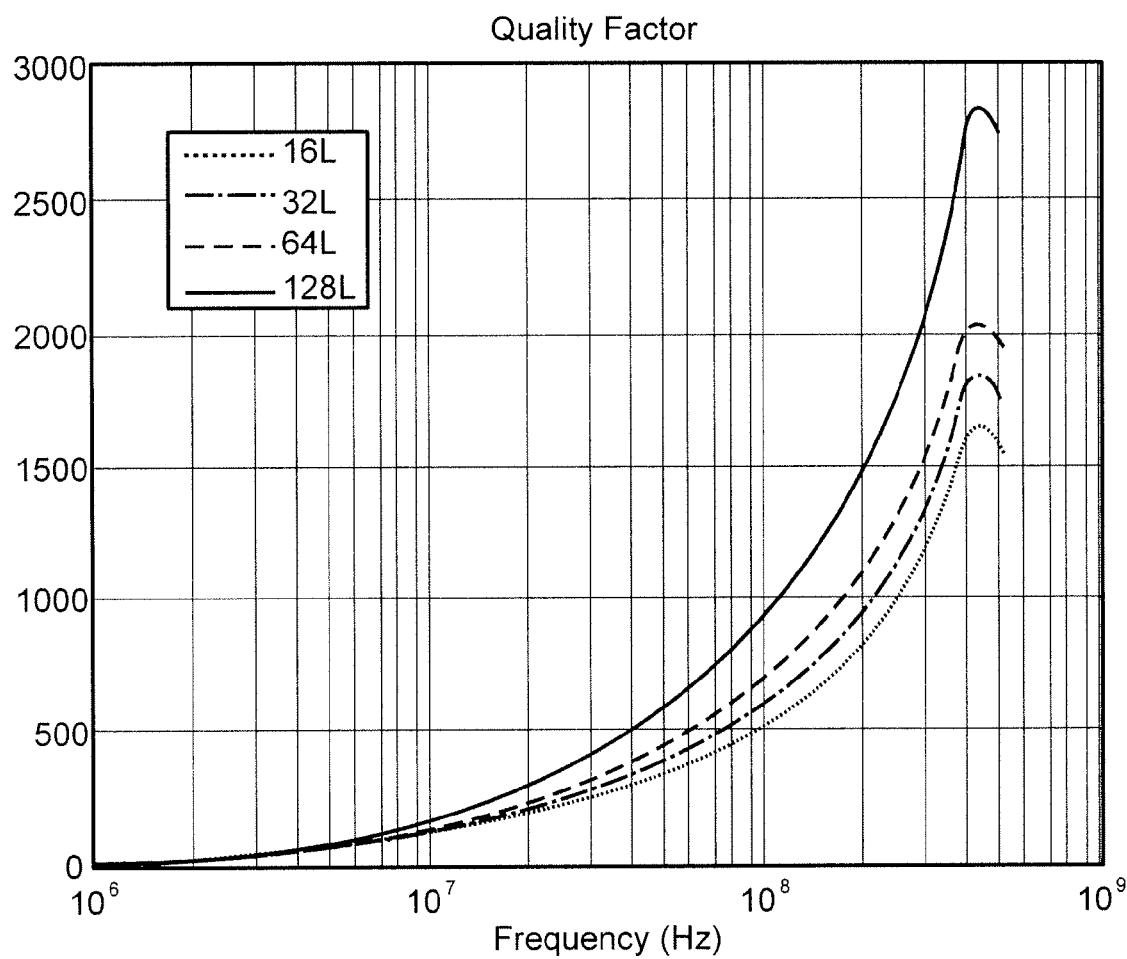
FIG. 12A is a graph illustrating the quality factor as a function of frequency.
Figure 12B:
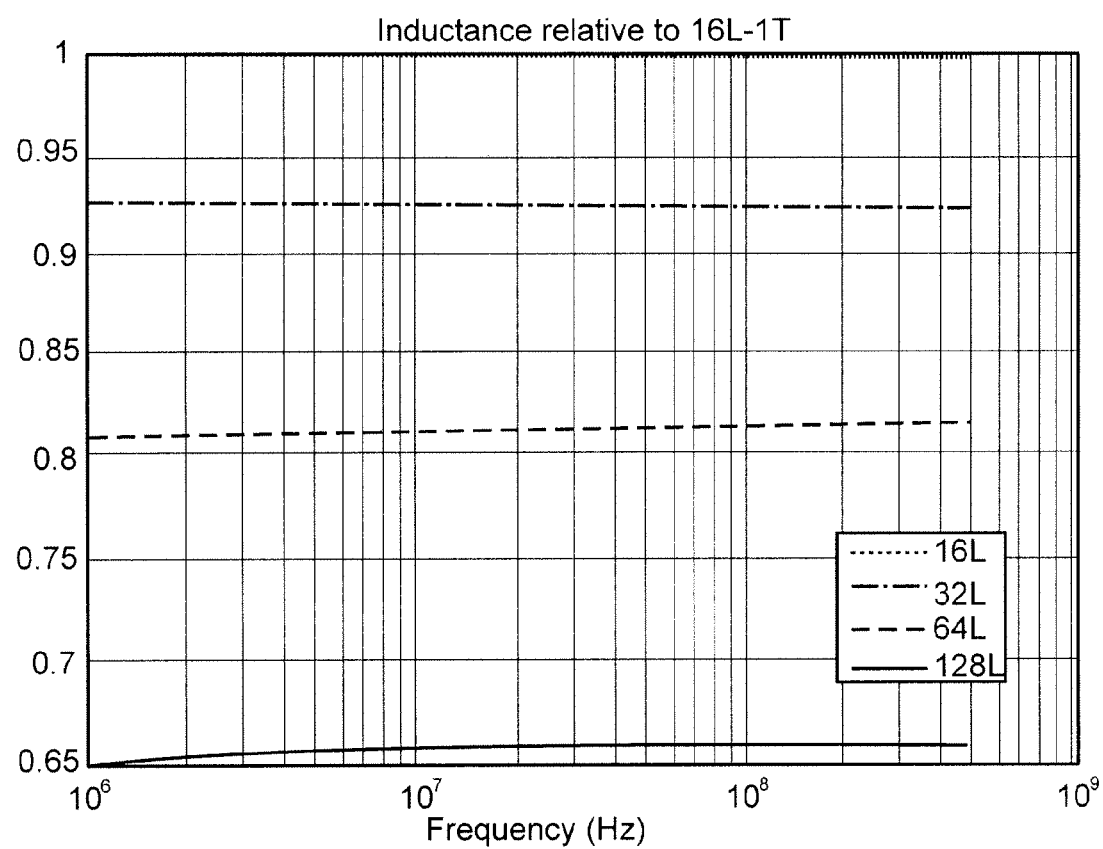
FIG. 12B is a graph illustrating the inductance relative to a 16 layer coil as a function of frequency.
Figure 12C:
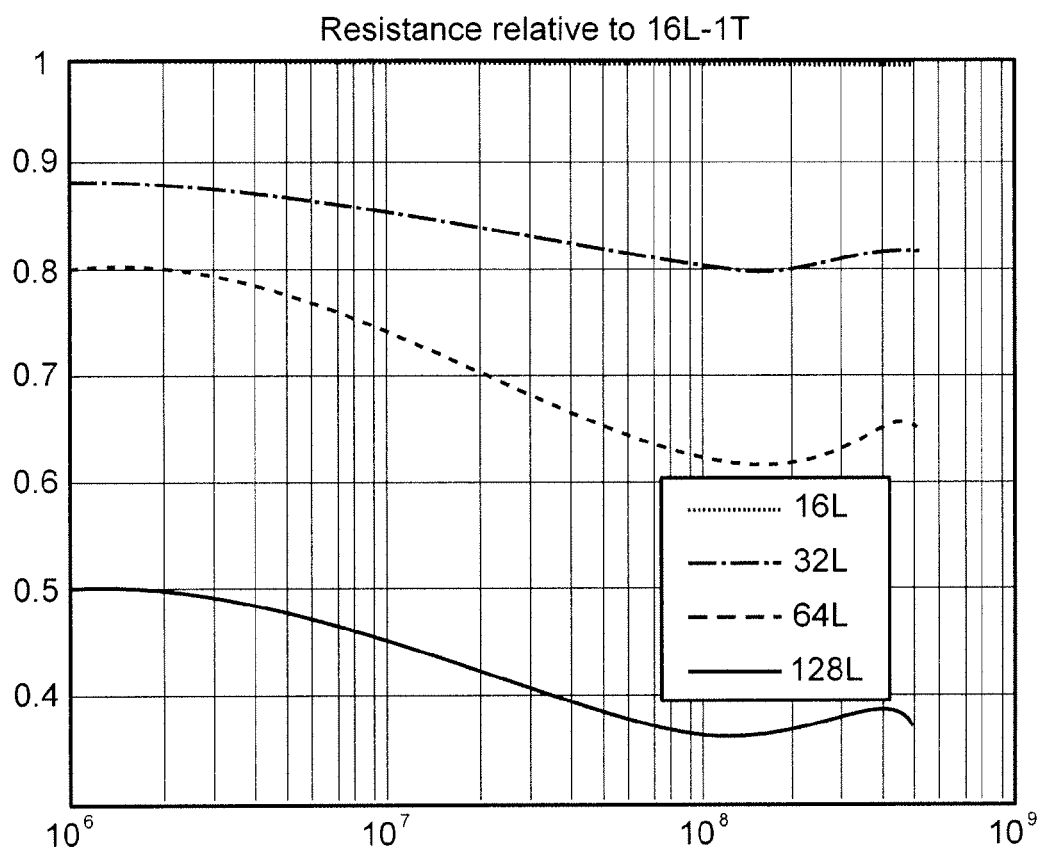
FIG. 12C is a graph illustrating the resistance relative to the 16 layer coil as a function of frequency.

FIGS. 12A-C are graphs illustrating the performance parameters and trends.

FIG. 12A is a graph illustrating the quality factor as a function of frequency. FIG. 12B is a graph illustrating the inductance relative to a 16 layer coil as a function of frequency. FIG. 12C is a graph illustrating the resistance relative to the 16 layer coil as a function of frequency. As can be seen in FIG. 12A, the quality factor improves with an increasing number of layers with relatively larger quality factors at higher frequencies. This is further shown in FIGS. 12B-C where it is shown that where the inductance is relatively constant (as compared to a 16 layer 1 turn coil) with frequency, while the resistance decreases as frequency increases as shown by the troughs around 100 MHz in FIG. 12C. The peak quality factor goes up to approximately 2900 at around 450 MHz.

Figure 13A:
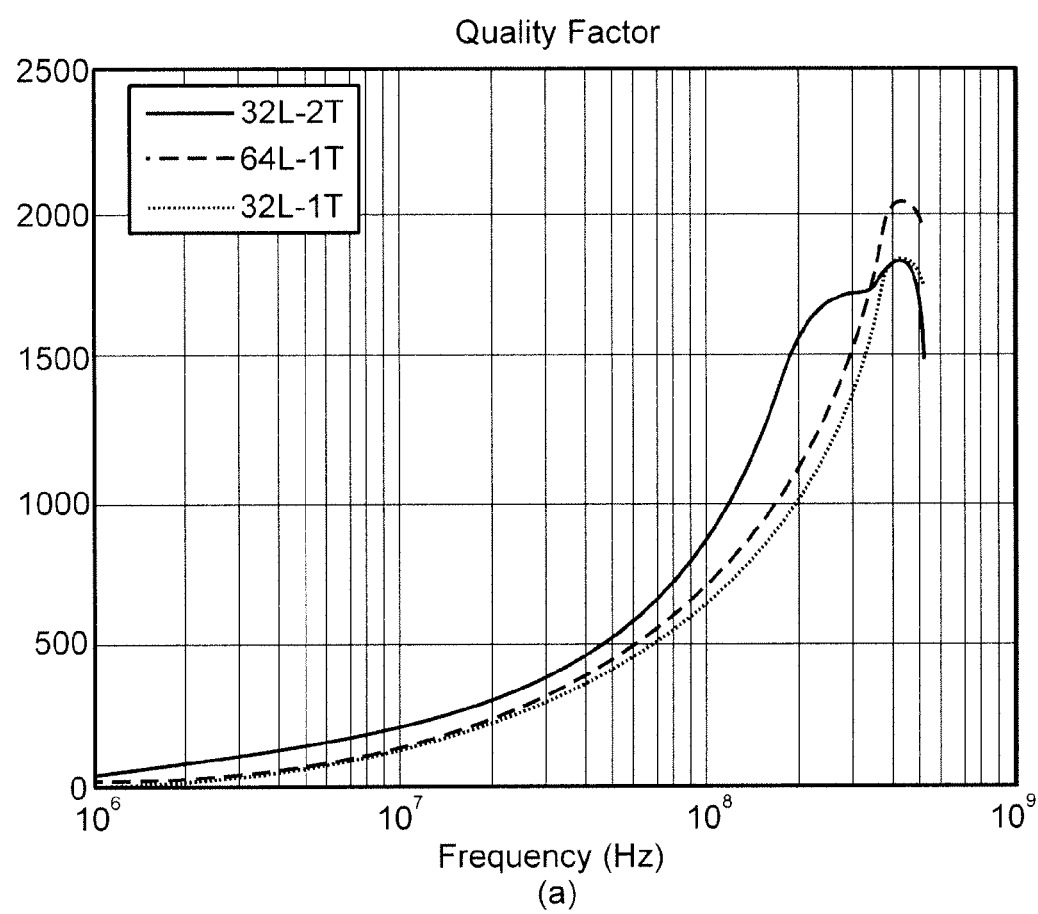
FIG. 13A is a graph illustrating the quality factor as a function of frequency.
Figure 13B:
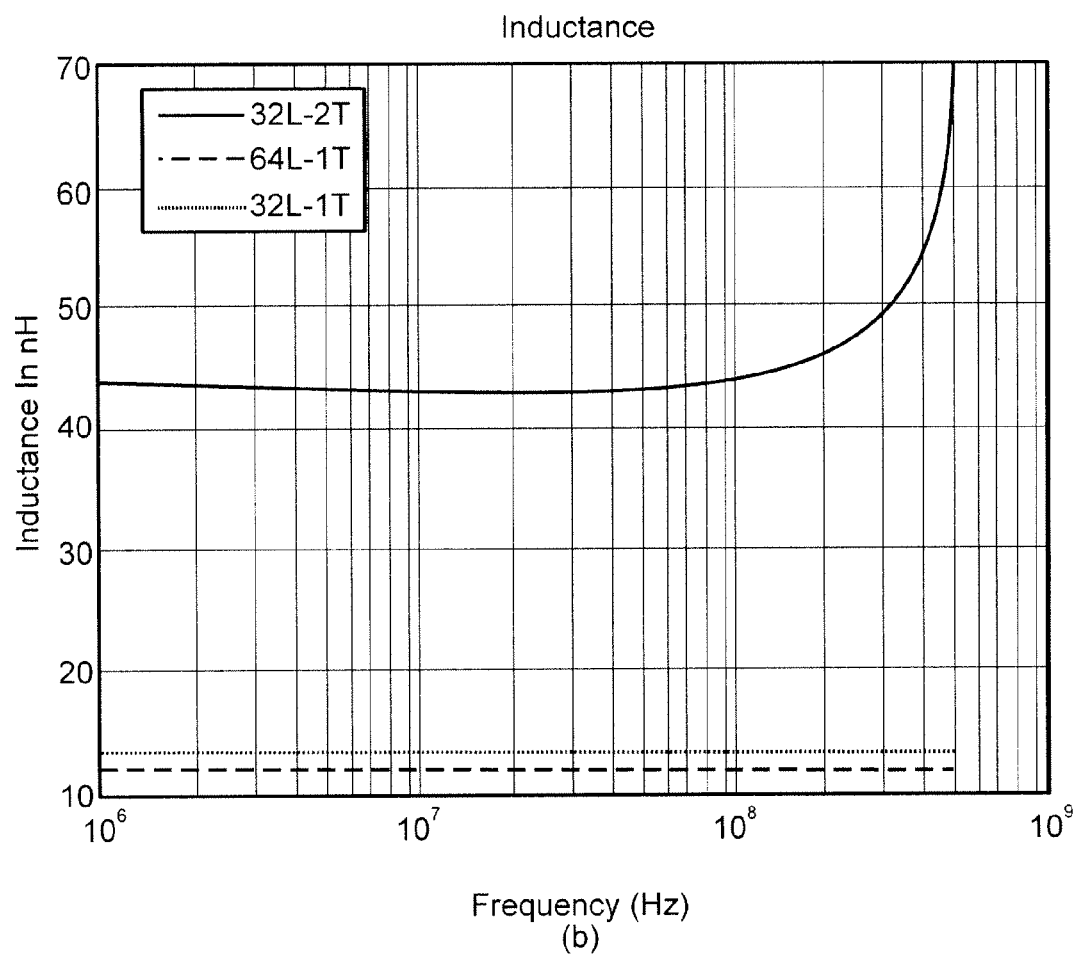
FIG. 13B is a graph illustrating the inductance as a function of frequency.
Figure 13C:
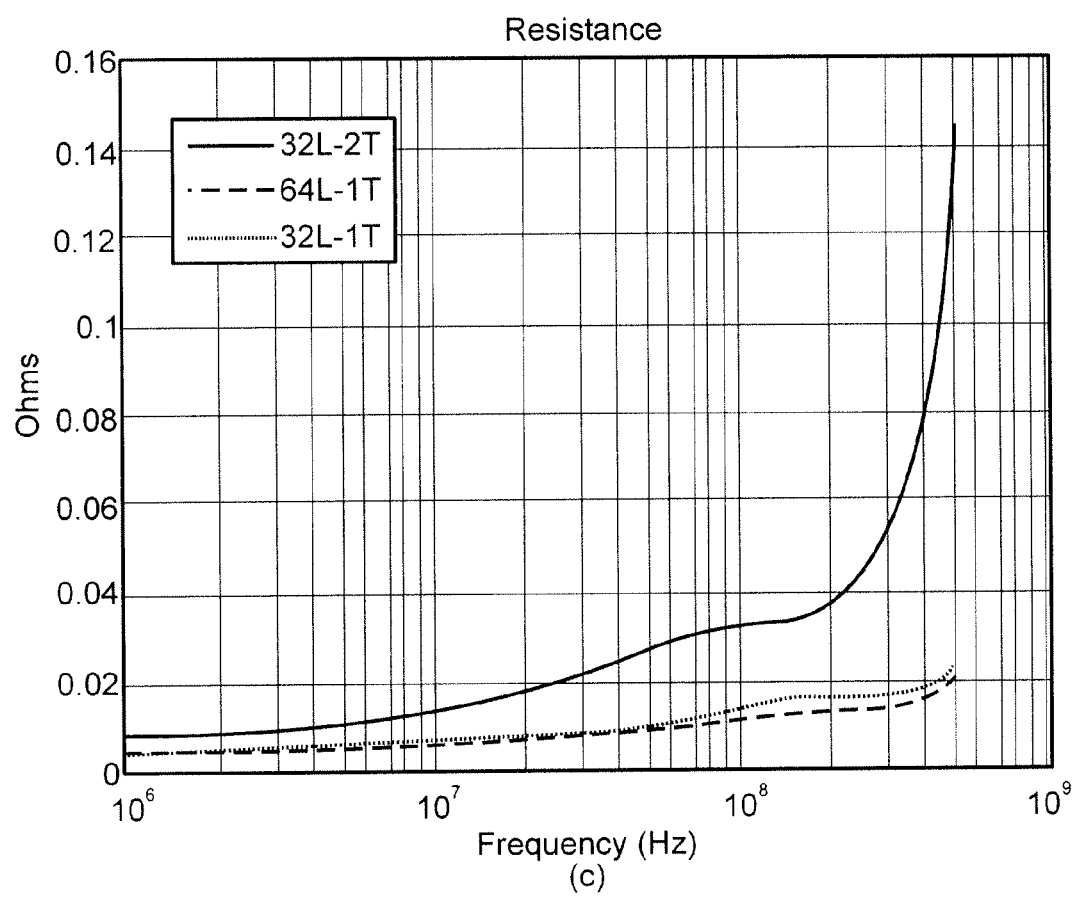
FIG. 13C is a graph illustrating the resistance as a function of frequency.

In yet another example, all design parameters are the same as in the preceding example for a 32 layer wire, except the number of turns is doubled, resulting in a double turn circular coil. The inductance and resistance for this 32 layer, double turn antenna increase between 3-3.5 times and 1.7-3 times, respectively, over the 32 layer, single turn antenna in the frequency range of 1 MHz to 200 MHz. FIGS. 13A-C are graphs illustrating the performance parameters and trends for this 32 layer, double turn antenna compared to the 32 and 64 layer, single turn antennas in the preceding example. FIG. 13A is a graph illustrating the quality factor as a function of frequency. FIG. 13B is a graph illustrating the inductance as a function of frequency. FIG. 13C is a graph illustrating the resistance as a function of frequency. As can be seen in FIGS. 13A-C, for the 32 layer, double turn antenna at frequencies below about 200 MHz, the inductance is nearly constant and the resistance follows trends similar to the single turn antennas. At frequencies greater than 200 MHz, both the inductance and resistance rise rapidly due to the contribution of parasitic capacitance, which is explained below. Even though the quality factor remains high at frequencies greater than 200 MHz, there may be significant electric fields present due to the capacitive effect, which may not be acceptable in some applications.

As noted above, an antenna may display parasitic effects. Associated with the antenna is a parasitic capacitance that is frequency dependent and whose contribution to the overall impedance increases with frequency. As a result of the parasitic capacitance, there exists a self-resonance frequency for the antenna beyond which the antenna behaves like a capacitor. To prevent the onset of parasitic capacitance, the antenna may be designed such that the inductance is nearly unchanging around the frequency of operation. Preferably, the slope of the reactance versus frequency graph is nearly linear (around the frequency of operation) with slope, $\partial X/\partial \omega \sim L$ (where X is the reactance, and L is the inductance that was designed for). Operating the antenna in this regime ensures that the parasitic coupling via electric fields is kept to a minimum. It is understood that that the X versus $\omega$ may not be perfectly linear due to other effects such as current crowding, proximity and skin effects.

Figure 14A:
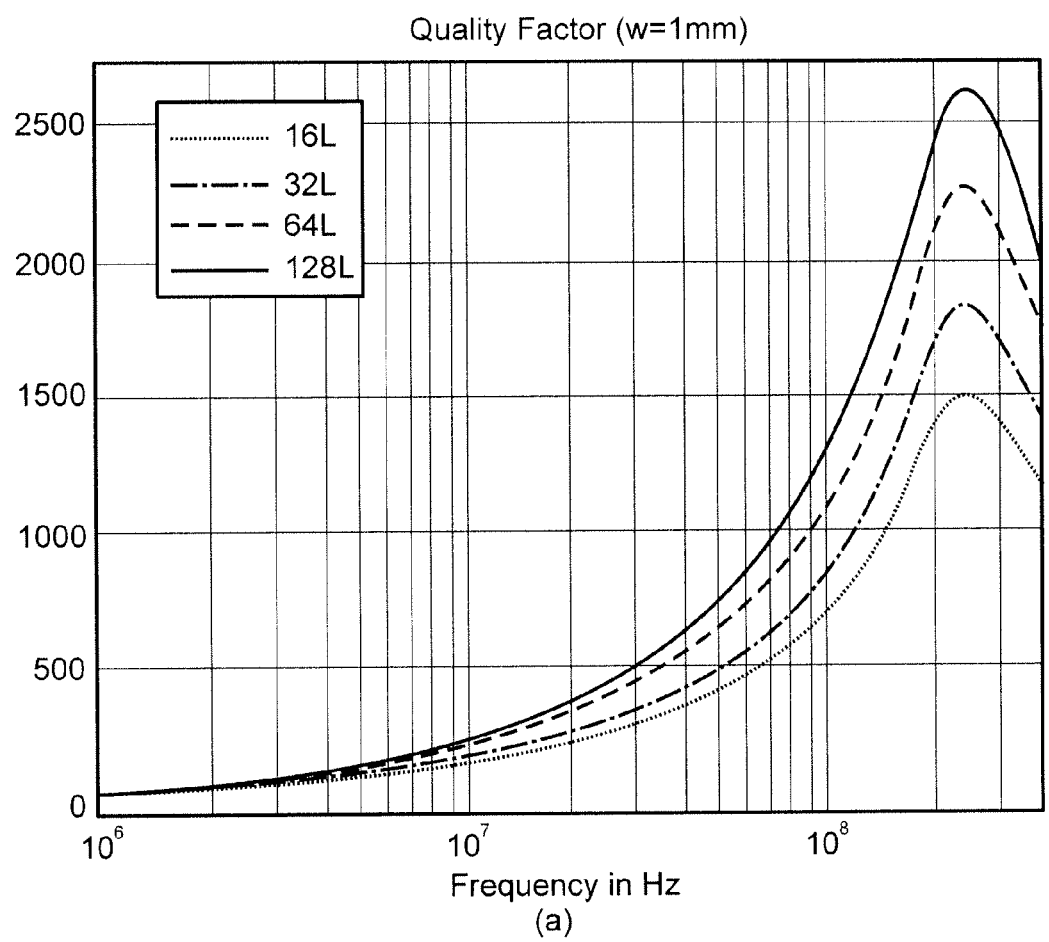
FIG. 14A is a graph illustrating the quality factor as a function of frequency for a coil having a metal strip width of 1 mm.
Figure 14B:
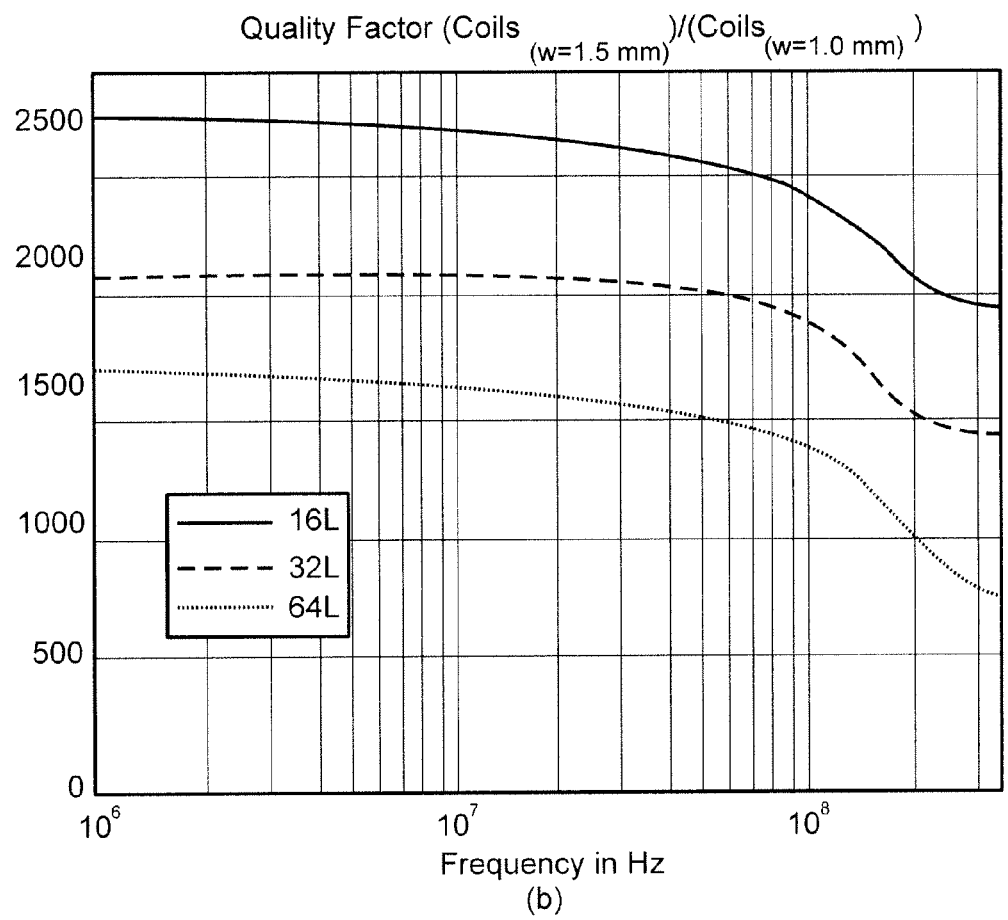
FIG. 14B is a graph illustrating the relative increase in quality factor for a coil having a metal width of 1.5 mm.
Figure 14C:
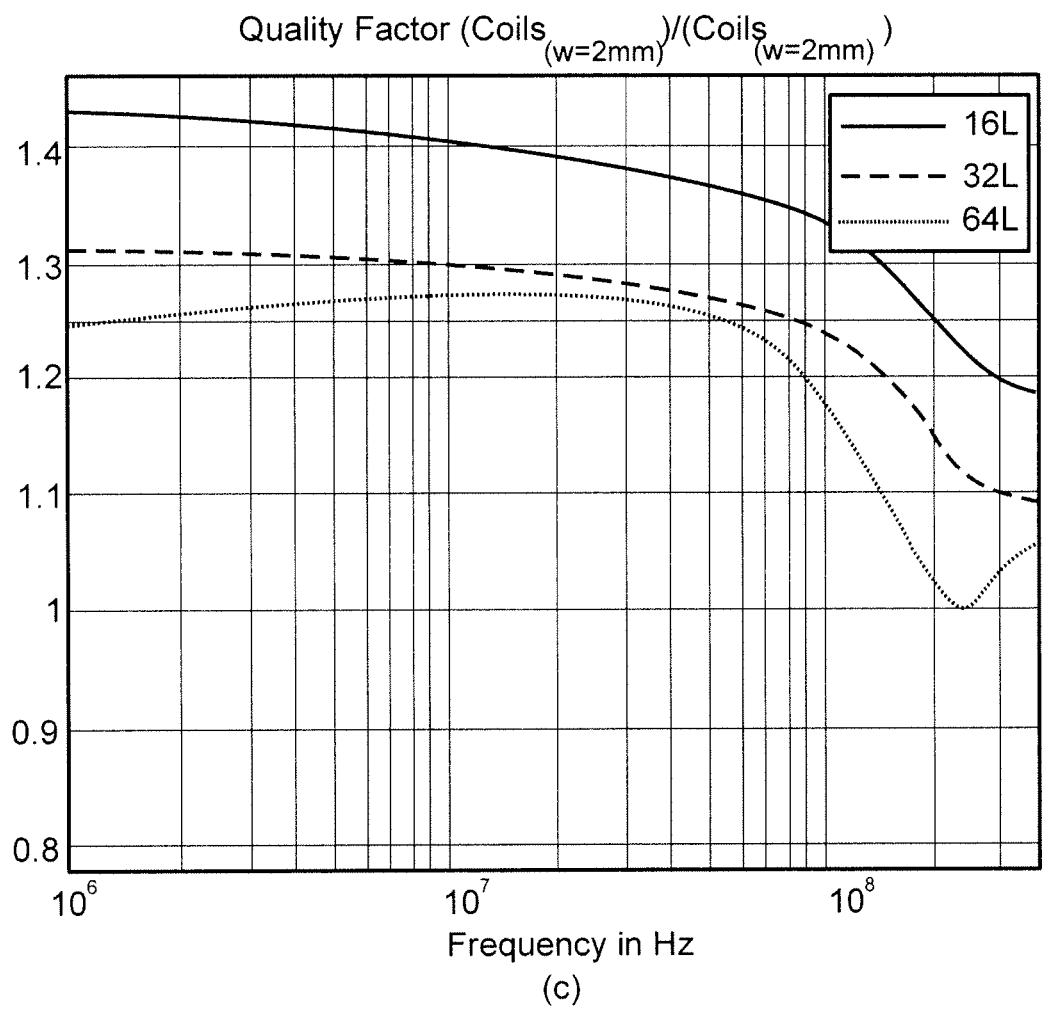
FIG. 14C is a graph illustrating the relative increase in quality factor for a coil having a metal width of 2 mm.

It is also contemplated that other designs may be used for the antenna in order to achieve higher quality factors. For example, for a single turn circular coil of multi-layer wire that may have between 16 and 128 layers, such as 16, 32, 64, or 128 layers, the coil may include a metal strip width of approximately 1 mm, a metal thickness of approximately 0.01 mm, an insulating layer of approximately 0.01 mm, and an outer radius of approximately 10 mm. Increasing the width of the metal reduces the resistance and the inductance, resulting in a higher quality factor. Due to the overall large size of the antenna (outer radius ~10 mm), the relatively small increase in the width (w) does not reduce the inductance. It should be noted that the same increase in metal width for a smaller antenna, such as, for example, with outer radius approximately 5 mm, the decrease in inductance would have been higher. FIGS. 14A-C are graphs illustrating the quality factors as a function of frequency for this example with a metal strip width of approximately 1 mm, 1.5 mm and 2 mm, respectively. In this example, the quality factor at 379 MHz is approximately 1425 for a metal strip width of 1 mm. Increasing the metal strip width to 1.5 mm and 2 mm increases the quality factor to approximately 1560 and 1486, respectively.

It should be noted that all the QF values mentioned above for the inductors are in free space (conductivity=0, relative permittivity=1). It is expected that the presence of a real world environment will affect the QF. For example, an antenna with a QF ~400 in free space, could have the QF change to about 200-300 when it is placed next to the human body. Further, if the antenna is placed inside the human body with little or no insulating coating, the QF might further change to less than 200. Applying a coating sufficiently thick or enclosing in a sufficiently large package before placing inside the human body might decrease the change in the QF of the antenna. It is expected that similar changes in QF characteristics will occur in any medium and in the proximity of any material, with the deviation from free space depending on the electrical properties of the material/medium and the distance from it.

As will be discuss herein, utilization of near-field communication for wireless transmission and/or reception can be applied to energy, power or data networks.

Energy Networks

Figure 15:
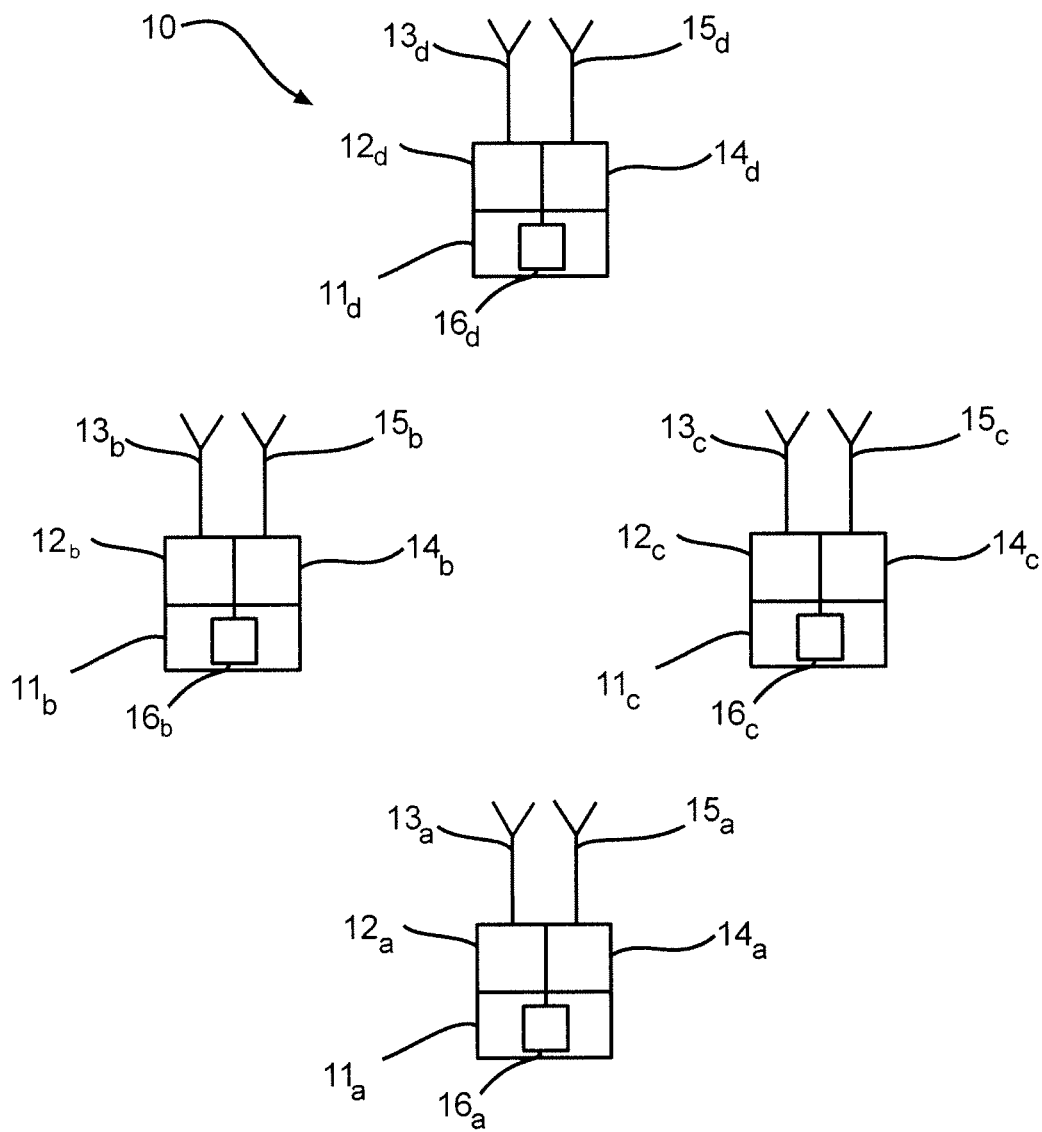
FIG. 15 illustrates a high-level block diagram of a near-field energy network.

An energy transfer network may be developed according to the present teachings. FIG. 15 illustrates a high-level block diagram of a near-field energy network 10. The network 10 includes a plurality of devices 11$_{a-d}$ (generally referred to as device 11). Each device 11 may include a transceiver. The transceiver may include a transmitting unit 12$_{a-d}$ and a receiving unit 14$_{a-d}$ for wireless communications. Although each transceiver may include a transmitting unit 12 and a receiving unit 14, it is understood that the transceiver may comprise only a transmitting unit 12 or only a receiving unit 14. Further, it is understood that the transmitting unit 12 and the receiving unit 14 in the transceiver may share certain or all circuit elements or may have separate and distinct circuit elements. Further, the transmitting unit 12 and/or receiving unit 14 may be coupled to a load 16. The load 16 may comprise of components within the device 11, outside the device 11, or a combination of components within and outside the device 11.

Each transmitting unit 12 includes a transmitting antenna 13. The transmitting antenna 13 has a resonant frequency $\omega$ and preferably has minimal resistive and radiative losses. The load 16 may include driver circuitry to generate signals to drive the transmitting antenna 13. Based on the received signals, the transmitting antenna 13 may produce a near-field in all directions (omni-directional) or may produce a near-field targeted towards a specific direction (directional). The targeted near-field may be produced through shielding, such as by ferrite materials. Of course, it is understood to those skilled in the art that other materials may be used to provide targeted near-fields.

Each receiving unit 14 includes a receiving antenna 15. A single antenna may be used for both the receiving antenna 15 and the transmitting antenna 13 or a separate antenna may be used for the receiving antenna 15 and the transmitting antenna 13. Each antenna 13, 15 has a resonant frequency (referred to as $\omega_a$-$\omega_d$). If separate transmitting and receiving antenna are used, it is preferred that the resonant frequency of the receiving antenna 15 is equal to the resonant frequency of the transmitting antenna 13.

When a receiving unit 14 of one device 11 (e.g., receiving unit $14_b$ of device $11_b$) is placed in the near-field of the transmitting unit 12 of another device 11 (e.g., transmitting unit $12_a$ of device $11_a$), an electromagnetic field generated by the transmitting unit $12_a$ will interact with the receiving unit $14_b$. If the resonant frequency of a receiving unit 14 (e.g., receiving unit $14_b$ of device $11_b$ having resonant frequency $\omega_b$) is the same as the resonant of the transmitting unit 12 (e.g., transmitting unit $14_a$ of device $11_a$ having resonant frequency $\omega_a$), the reactive electromagnetic fields of the transmitting unit 11a will induce an alternating current within the receiving unit $14_b$. The induced current may be used to provide power or convey data to load $16_b$. As a result, device $11_b$ is able to absorb energy from device $11_a$. It is understood that any number of devices having a resonant frequency equal to the resonating frequency of the transmitting device (e.g., $\omega_b$) may be added to the near-field energy network and draw energy from the transmitting device, provided that the resonant frequency of the transmitting unit $12_a$ is not significantly altered due to the loading effect of the added devices.

If the resonant frequency of a receiving unit 14 (e.g., receiving unit $14_c$ of device $11_c$ having resonant frequency $\omega_c$) is different than the resonant of the transmitting unit 12 (e.g., transmitting unit $12_a$ of device $11_a$ having resonant frequency $\omega_a$), the receiving unit $14_c$ will have a high impedance to the transmitting unit $12_a$ and will draw little energy from the transmitting unit $12_a$.

It is understood that the amount of energy transferred from a transmitting unit $12_a$ to receiving unit $14_c$ depends on many factors, including intrinsic losses in the transmitting unit $12_a$ and receiving unit $14_c$ and the transfer of energy to other devices such as receiving unit $14_b$. Also significant are the proximity of $\omega_a$ and $\omega_c$ and the width of the resonant bands in each device. FIGS. 16A-F illustrates graphs showing how various factors affect the transfer of energy.

Figure 16A:
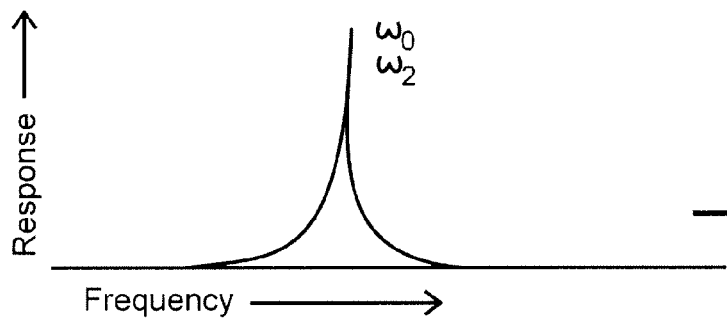
FIG. 16A illustrate a graph showing a situation where the receiving unit and transmitting unit have identical resonant frequencies the bands narrow.
Figure 16B:
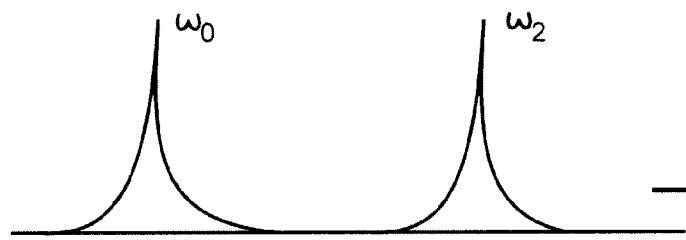
FIG. 16B illustrates a graph showing a situation where the receiving unit and transmitting unit have different resonant frequencies the bands narrow.
Figure 16C:
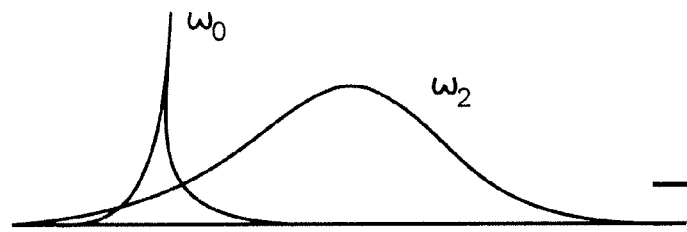
FIG. 16C illustrates a graph showing a situation where the receiving unit and transmitting unit have different resonant frequencies and the receiving unit has a wide resonant.
Figure 16D:
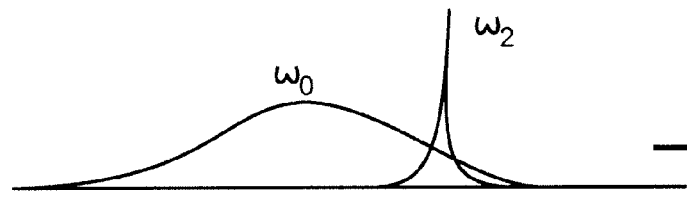
FIG. 16D illustrates a graph showing a situation where the receiving unit and transmitting unit have different resonant frequencies and the transmitting device is lossy.
Figure 16E:
FIG. 16E illustrates a graph showing a situation where the receiving unit and the transmitting unit have resonant frequencies that are far apart and both the transmitting unit and the receiving unit are lossy.
Figure 16F:
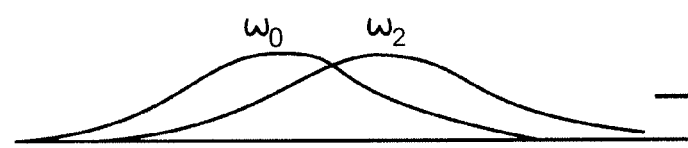
FIG. 16F illustrates a graph showing a situation where the receiving unit and the transmitting unit have resonant frequencies that are close and both the transmitting unit and the receiving unit are lossy.

FIG. 16A illustrates a situation where $\omega_a$ and $\omega_c$ are identical and the bands narrow. This represents an ideal scenario and the case of maximum power transfer efficiency. FIG. 16B illustrates a situation where $\omega_a$ and $\omega_c$ are different and the bands narrow. No energy is transferred in this scenario. FIG. 16C illustrates a situation where $\omega_a$ and $\omega_c$ are different and receiving unit $14_c$ has a wide resonant. A wider resonant band occurs when an antenna has higher resistive and radiative losses. Receiving unit $14_c$ has more impedance to $\omega_a$ than in the situation shown in FIG. 16B, but is still able to absorb some energy from transmitting device $11_a$. FIG. 16D illustrates a situation where $\omega_a$ and $\omega_c$ are different and transmitting device $11_a$ is lossy. Resistive and radiative losses in transmitting device $11_a$ lead to a wide resonant band. A smaller portion of the antennas energy is available for transfer to receiving unit $14_c$. FIG. 16E illustrates a situation where $\omega_a$ and $\omega_c$ are far apart and both the transmitting unit $12_a$ and the receiving unit $14_c$ are lossy. Here, no energy is transferred from the transmitting unit $12_a$ to the receiving unit $14_c$. FIG. 16F illustrates a situation where $\omega_a$ and $\omega_c$ are close and both the transmitting unit $12_a$ and the receiving unit $14_c$ are lossy. Energy is transferred between the transmitting unit $12_a$ and the receiving unit $14_c$ but the system is inefficient due to high losses.

Many common everyday objects are conductive (e.g., steel cabinets, and automobiles) and will have frequency responses similar to receiving unit $14_c$ in FIG. *16C (but wider because of greater resistive losses). These objects are thus able to absorb some energy from transmitting unit $12_a$ and contribute to losses in the system. Thus far, only the general transfer of energy has been discussed, however, the use of the energy may vary by application, but broadly may be for either the transfer of power or the transfer of data.

Power Networks

A power transfer network may be developed according to the present teachings. When a receiving unit $14_b$ is placed within the near-field of a transmitting unit $12_a$ and the resonant frequency of the receiving unit $14_b$ (i.e., $\omega_b$) is approximately equal to the resonant frequency of the transmitting unit 12a ($\omega_a$), energy will transfer from the transmitting unit $12_a$ to the receiving unit $14_b$. If multiple receiving devices (e.g., $11_b$-$11_d$), all having a resonant frequency equal to the resonant frequency of the transmitting unit $12_a$ (i.e., $\omega_a$), are placed in the near-field, each receiving device (e.g., $11_b$-$11_d$) will draw energy from the transmitting unit $12_a$ in the form of an alternating current. The receiving devices $11_a$-$11_d$ may include a transducer which may use the induced alternating current to store energy in a power storage device, such as battery or capacitor. Alternatively, the transducer may use induced alternating current to directly power electronic components within or couple to the receiving device (e.g., $11_b$-$11_d$).

Figure 17:
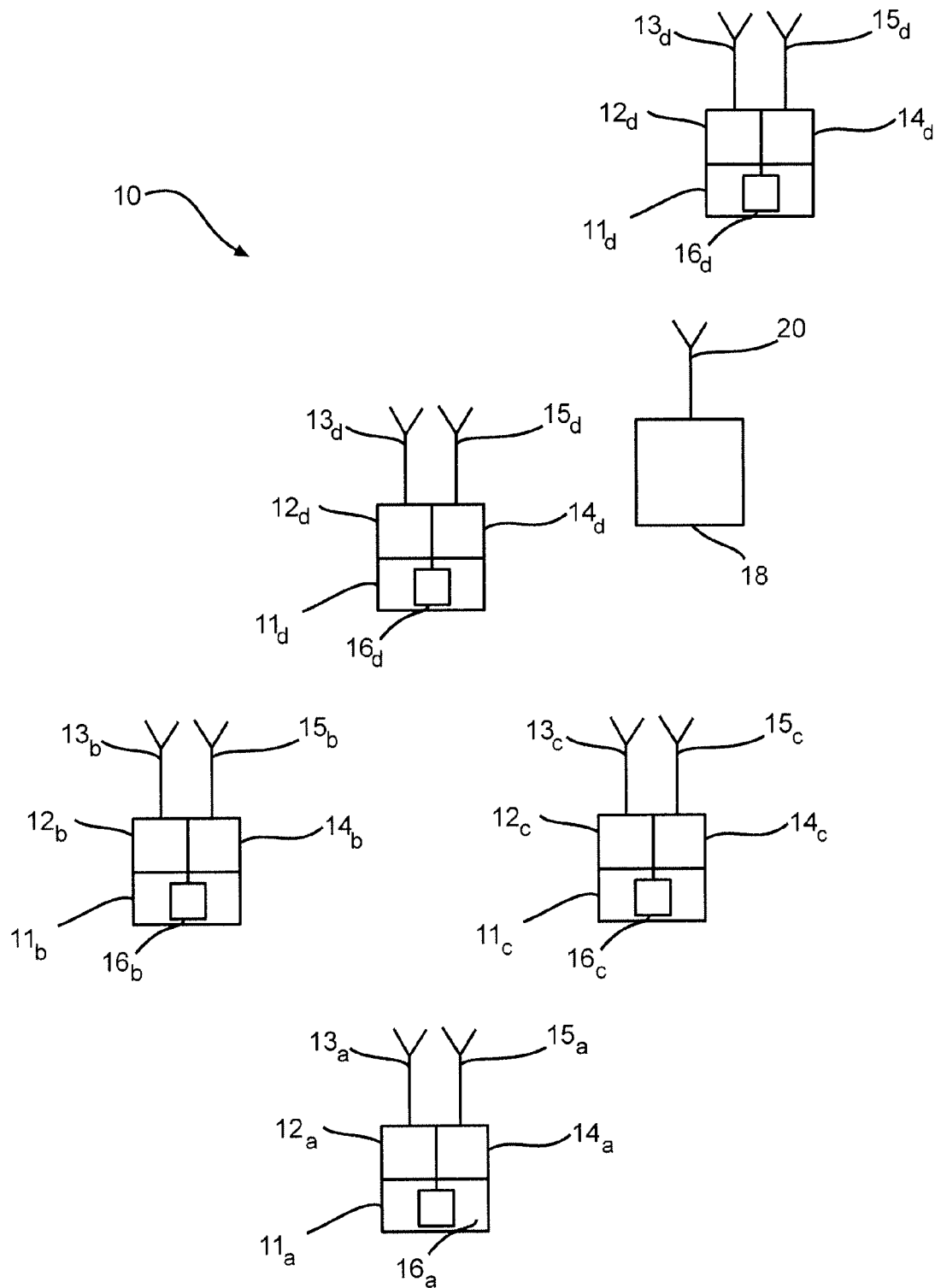
FIG. 17 illustrates a high-level block diagram of a near-field energy network with repeaters.

It is understood that it may not be possible to place all transmitting and receiving devices (e.g., $11_b$-$11_d$) within the near-field of the transmitting unit $12_a$. As illustrated in FIG. 17, in order to deliver energy to receiving devices 11 outside of the near-field (e.g., receiving unit $11_c$) one or more repeaters 18 may be used. The one or more repeaters 18 may contain an antenna 20 which is tuned to $\omega_a$. The repeater 18 may draw energy from the transmitting unit 12 via the antenna 20 in the form of an induced current. The one or more repeaters 18 may use the induced current to produce a second energy field using the antenna 20. Alternatively, the second energy field may be produced using a second antenna (not shown). The second energy field may be used to induce an alternating current in the receiving unit $14_c$. The receiving unit $14_c$ may include a transducer which may use the induced alternating current to store energy in a power storage device, such as battery or capacitor. Alternatively, the transducer may use induced alternating current to power electronic components within the receiving unit $14_c$. It is understood that the antenna 20 or second antenna (not shown) may produce a near-field in all directions (omni-directional) or may produce a near-field targeted towards a specific direction (directional).

Data Networks

A data transfer network may be developed according to the present teachings. A network designed for data transfer would be similar to the power networks described previously, except that the signal transmitted by the transmitting devices in the network may be modulated time-varying signals which carry data. There are several possible general layouts for a data-network.

One example of a data network layout includes one or more receiving units ($14_{b-d}$) placed within the near-field of a transmitting unit $12_a$. Each of the receiving units ($14_{b-d}$) may be capable of communicating to the transmitting unit $12_a$ and/or other receiving units 14. It is understood that receiving units which may be out of near-field of the transmitting unit 12 may be reached using one or more repeaters 18 in the manner described above. In another example, a receiving unit 14 may be placed far-field of the transmitting unit 12 and utilize the radiative field of the transmitting unit 12 for communication.

Such far-field communication is achieved in a manner similar to far-field communication techniques known to those of ordinary skill in the art.

The devices 11 within the networks may be designed to handle data-transfer in several ways. For example, the devices 11 and their antennas 13, 15 may be designed to (1) receive data only; (2) transmit data only; or (3) receive and transmit data, using either a shared antenna for receiving and transmitting or separate and dedicated antennas for receiving and transmitting. In addition, the devices 11 may be designed to handle both data- and power-transfer. In such situations, each device 11 may be designed to: (1) transfer data only; (2) transfer power only; (3) transfer data and power, where each device 11 may use any combination of sending/receiving data and sending/receiving power, each device 11 has a shared antenna for data- and power-transfer, or each device 11 has separate, dedicated antennas for data- and power-transfer.

Each receiving unit 14 may have an electronic identification (ID) that is unique to that receiving unit 14 on the network 10. The ID acts as an identifier for a particular receiving unit 14 on the network and allows a receiving unit 14 on the network to identify other receiving units 14 on the network 10 for communication. To initiate a data-transfer session, a transmitting device would identify a receiving device with its ID and begin communications using an initiation instruction. The data transfer would occur using a specified modulation scheme. Security protocols may be used to ensure that the data transferred by and stored in the devices are secure and not accessible to unauthorized devices which are not present in the designed network 10.

Periodic data communication may occur between a transmitting unit 12 and one or more receiving units 14 or between a receiving unit 14 and one or more other receiving units 14. In transmitting unit-receiving unit communications, a transmitting unit 12 may identify a particular receiving unit 14 based on its ID and initiate a communication session. Alternative, a receiving unit 14 may identify a transmitting unit 12 based on its ID and initiate a communication session. The communication session may be terminated by either the transmitting unit 12 or the receiving unit 14.

In receiving unit-receiving unit communications, two receiving units 14 may connect directly with each other in direct communication. Alternatively, two receiving units 14 may connect with each other using the transmitting unit 12 as an intermediary. In such cases, each receiving unit 14 may connect to the transmitting unit 12 and the transmitting unit 12 would receive information from one receiving unit 14 and transmit it to the other receiving unit 14. In another alternative, two receiving units 14 may communicate using one or more repeaters 18 where the one or more repeaters 18 may receive a signal from a receiving unit 14 and transmit it to another receiving unit 14. The one or more repeaters 18 may be one or more stand-alone resonant antennae and may be independent of any circuitry.

The system and method illustrated in FIG. 15 and FIG. 17 to efficiently transfer energy between two or more devices may be used in a variety of applications in order to operate household appliances such as vacuums, irons, televisions, computer peripheral devices; mobile devices; military applications such as surveillance equipment, night vision devices, sensor nodes and devices; transportation applications such as sensors designed to monitor automobile or train performance and safety; aerospace applications, such as control of flaps, rudders, or landing gear; space technology; naval applications such as applications to power unmanned watercraft; traffic control applications such as road imbedded sensors; industrial applications; asset tracking such as RFID tags and transponders; robotic networks; and medical devices.

General Near-Field Power and Data Transfer System

As appreciated by the present teachings, near-field power and data transfer are derived from the same physical principles. When utilized together, near-field power and data transfer provide an opportunity to create a wide variety of systems. The following describes a general system for near-field power and data transfer.

An near field power and data network (also referred herein as a "NF-PDAT") may consist of multiple transmitting and receiving units. For the sake of simplicity, a simpler network consisting of a single transmitting unit 12 and a single receiving unit 14 is considered. The following description follows the path of the energy as it is transferred from the transmitting unit 12 to the receiving unit 14 and to a load coupled to the receiving unit 14.

Initially, the energy needed to drive the PDAT network must be obtained from a primary source. The primary source may be a main 50/60 Hz wall socket, a standard battery, a rechargeable battery connectable to a wall socket, or a rechargeable battery with indirect recharging. A wall-socket is one preferred method of obtaining energy because of its abundance in this form. In the event a device cannot be connected a wall socket, or portability is a requirement, batteries may be used. In addition, rechargeable batteries may be used. Rechargeable batteries may be replenished when their stored energy falls below a capacity. It is known that recharging allows batteries to be sued in devices that would otherwise drain batteries too quickly, have too little space for batteries of an appropriate size, or have limited access for replacing the battery. A primary source of power, such as a wall socket or another battery may be used to replenish battery life in the rechargeable battery. In most devices, recharging is typically accomplished by connecting the battery to a wall socket for a short period of time (e.g., laptops and cell-phones). In some applications (e.g., implanted medical devices), direct attachment to a power cord is not possible. In such situations, indirect recharging methods, such as inductive coupling to an external power source, have been used. It is understood that recharging may be accomplished by other methods. For example, if there exists a clear line-of-sight between the energy source and the device, an optical link, laser, or highly-directive radio-frequency beam may be used to transfer energy.

Alternative sources of energy may be used to power the system or to provide energy for components within the system (such as recharging a battery). These may include the conversion of one form of energy into electrical energy. One such example is the conversion of kinetic energy into electrical energy. This may be accomplished by converting movement into energy. For instance, a device attached to the body may use body movements to spin a rotor that causes a generator to produce an alternating current. Another example is the conversion of light energy into electrical energy. For instance, photovoltaic cells placed externally may convert sunlight or ambient room light into energy. In another example, changes in pressure may be converted into electrical energy. For instance, a piezoelectric appropriately placed on a device may be used to convert pressure changes (e.g. air pressure changes or direct pressure through contact) into electrical currents. In another example, thermal gradients may be converted into electrical energy. For instance, a thermo-electric generator (TEG) placed within a device may be used to convert a temperature gradient across the device into electrical energy. Such a TEG may be useful in devices that produce heat during their operation, as a portion of the heat energy could be converted into electrical energy.

The present teachings also include a method for designing a multi-layer multi-turn antenna for use in a high efficiency wireless power and data telemetry system. Given a certain frequency of operation, one or more of the following steps may be followed to design application-specific antennae:

1. Perform analytical calculations and system level simulations to obtain minimum required inductance for sufficient coupling coefficient
2. Based on analytical calculations (e.g., for coupling coefficient, induced voltage, etc), choose the number of turns required for the appropriate inductance
3. Select the conductor layer thickness to be about 2 times the skin depth or the minimum allowable based on the fabrication technology; whichever is higher.
4. Select the insulation thickness to be the minimum allowable by the fabrication technology or a larger thickness to achieve desired performance.
5. Select the maximum surface area possible (depends on the application). This area need not necessarily be square or circular. It could be any shape conforming to the overall system and could meander around other components.
6. Select the maximum number of layers possible depending on fabrication technology and the application.
7. Design a multi-layer multi-turn antenna in a numerical modeling tool (e.g., based on MoM or FDTD or FEM or MLFMM OR some other or combination of these) with the number of turns from step-1 and 2, and optimize (Steps 3-6) the number of layers and other parameters.
   a. Ensure that the Quality factor peak is obtained in the whereabouts of the selected frequency
   b. Ensure that the inductance for this quality factor is greater than or equal to the minimum allowable (from system level constraints)
   c. If required, ensure that the E-fields are minimized by keeping the parasitic capacitive effects low (refer to previous section)

The present teachings also include a method of manufacturing the antenna after the antenna is designed. The multi-layer multi-turn antenna utilizes strips of metal that may be deposited through a specific mask in, for example but not limited to, a PCB/ceramic/metal printing process or in a semiconductor foundry. An alternative method of fabricating the antenna may utilize conductive tape/ribbon/sheet/leaf with one or more tape/ribbon/sheet/leaf placed on top of each other separated by an insulating layer and shorting the multiple strips by soldering at the designated via locations. Another method of fabricating the antenna would be to cut out specific shapes from conductive sheets or "leaf" (for e.g. gold or copper leaf) and following steps that similar to that for the conductive tape/ribbon. A three dimensional printing process (such as that offered by Eoplex Technologies) may also be used in addition to metal deposition processes like physical vapor deposition, thin film deposition, thick film deposition and the like.

The present teachings lends itself to be incorporated with current fabrication techniques for multi-layer printed wiring board, printed circuit boards and semiconductor fabrication technologies with multi-layer interconnects. As advancements in fabrication techniques are made, it is expected that the multi-layer multi-turn antenna will likely benefit greatly from such improvements. This compatibility with conventional fabrication techniques will allow these antennas to be relatively easily incorporated into conventional circuit boards. Such advances may also provide accurate repeatability and small feature sizes (i.e., high resolution).

As noted above, the design and structure of the present system allows for extended range (i.e., the separation distance between a transmitting and a receiving wireless antenna). The increase in range enables power to be transferred across a greater distance, allowing the transmitter to be further away from the receiver. For example, in applications such as RFID, the tag read range for high frequency interrogators is no greater than 3 feet, which is insufficient for certain applications, such as pallet tracking. The wireless antenna of the present system offers an improvement for pallet tracking via RFID by delivering the concentrated power that this particular application requires to facilitate reflecting the interrogator signal needed for better extended read range performance. In other applications such as military systems, the extended range provided by the present invention enables transfer of power to devices in difficult to reach locations, or to devices in harsh environments. In consumer electronics the extended range allows for the user to charge or transfer energy to a device from a more convenient location.

The present system also enables multiple operational needs from a single design concept, namely, the multi-layer multi-turn antenna. The present system may serve as a receiver antenna, a source antenna, a transceiver (acting as a source and a receiver), and as a repeater antenna. Alternatively, the design may be used for inductor designs solely as a lumped element in a circuit (e.g., in RF filters circuits, RF matching circuits).

Figure 20:
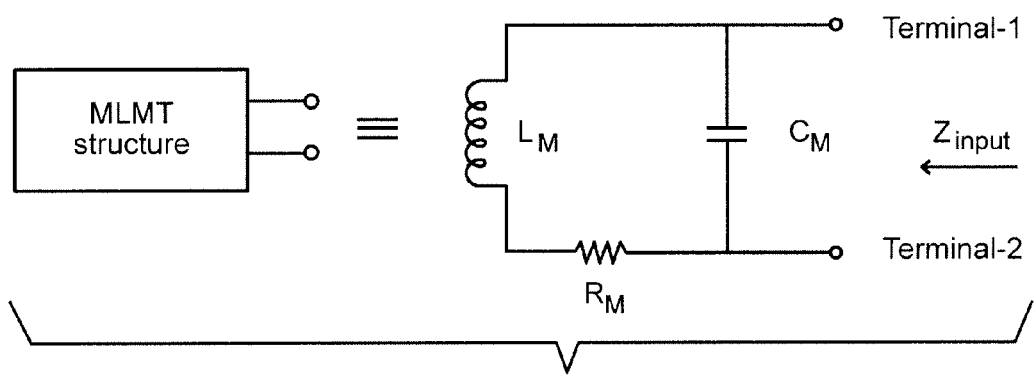
FIG. 20 illustrates an equivalent circuit diagram of any MLMT structure.

The MLMT antenna structure of the present invention may be represented in various circuit design embodiments. An equivalent circuit diagram for the MLMT antenna structure is given in FIG. 20. It comprises the following parameters:

$L_M$=Intrinsic Inductance
$C_M$=Intrinsic Capacitance
$R_M$=Intrinsic Resistance The characteristics of the MLMT antenna embodiment depend on the design values of $L_M$, $R_M$, and $C_M$; the operating center frequency and additional components that are placed across Terminal 1 and Terminal 2.

Let the angular frequency of operation be ω. The input impedance, $Z_{input}$ of the MLMT antenna embodiment then is given in general terms by equation 1(c) based on 1(a) and 1(b)

$$Z1 = \frac{1}{j \cdot \omega \cdot C_M} \quad \text{Equation 1(a)}$$

$$Z2 = R_M + j \cdot \omega \cdot L_M \quad \text{Equation 1(b)}$$

$$Z_{input} = \frac{Z1 \cdot Z2}{Z1 + Z2} \quad \text{Equation 1(c)}$$

Figure 21:
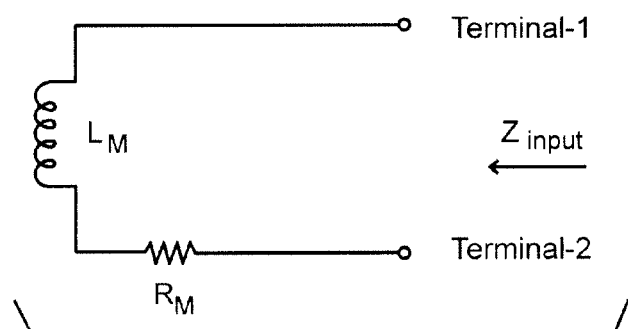
FIG. 21 illustrates an equivalent circuit diagram for an MLMT structure operating as an inductor (condition 1)

The MLMT antenna structure of the present invention then can be represented in various circuit design embodiments. For example, the MLMT antenna structure can be operated in three modes:

Mode 1: as an inductor such as embodied in a lumped circuit element, when condition 1, which is given by equation 2(a), is satisfied resulting in equation 2(b). The equivalent circuit diagram is given in FIG. 21.

$$Z1 >> Z2 \quad \text{Equation 2(a)}$$

$$Z_{input} \approx Z2 \quad \text{Equation 2(b)}$$

Figure 22A:
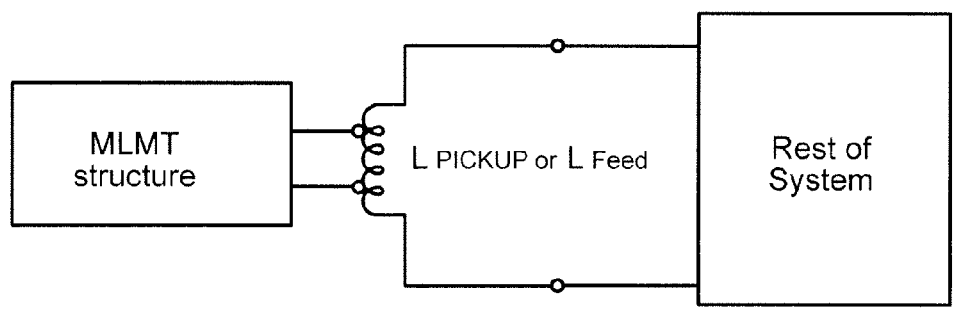
FIG. 22A illustrates an equivalent circuit diagram for an MLMT structure operating as a self-resonator in a circuit (Type 1)
Figure 22B:
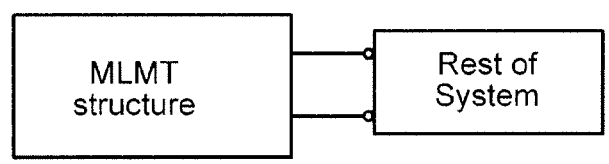
FIG. 22B illustrates an equivalent circuit diagram for an MLMT structure operating as a stand alone self-resonator (Type 1)

Mode 2: as a resonator such as embodied in a stand-alone tank circuit or embodied in an HF and/or RF circuit, where the resonator may be one of two types Type 1: as a self-resonator, when condition 2, given by equation 3 is satisfied. The equivalent circuit diagrams are given in FIGS. 22A and 22B $$\omega^2 \cdot L_M \cdot C_M \approx 1 \qquad \text{Equation 3}$$

Type 2: as a resonator, where resonance is achieved by adding a capacitor, $C_{ADDED}$, in series or parallel. The equivalent circuit diagrams showing series and parallel capacitor additions are given in FIGS. 23A and 23B. The Mode 2 Type 2 circuit diagrams are given in FIGS. 24A, 24B, and 24C.

In both Type 1 and Type 2, $L_{Pickup}$ and $L_{feed}$ refer to a pickup inductor and a feed inductor, respectively. These are coils which have an inductance that is smaller than the inductance value of the MLMT structure, $L_M$, and have a certain coupling to the MLMT structure. The coupling may be varied to achieve the desirable matching conditions for power transfer to or from the MLMT structure from or to the rest of the system. For simplicity and proof of concept, the embodiments described herein provide a single capacitor, $C_{ADDED}$ example for achieving resonance for illustration purposes. In a practical circuit, a more complex circuit comprising multiple capacitors and/or inductors and/or resistors may be used. All embodiments shown in FIGS. 22 and 24 may be used on the transmitter side and/or on the receiver side of the system.

Mode 3: as a capacitor, when condition 3, given by equation 4 is satisfied $$\omega^2 \cdot L_M \cdot C_M > 1 \qquad \text{Equation 4}$$

The unique arrangement of the layers and customized wire segmentation in the present system compared with existing design technologies demonstrates improved system performance in similar and smaller packaging volumes as shown by quality factors that are more than 2 times higher than those realized from existing technologies. By combining material with specific properties, specifying shapes, lengths, and thicknesses and defining layer order, the present system permits pairing of the inductance and quality factor with a specific application to optimally achieve a desired response, including, but not limited to, wireless tissue stimulation, wireless telemetry, wireless component recharging, wireless non-destructive testing, wireless sensing, and wireless energy or power management.

Another specific advantage of the present system is that it enables a more efficient means of Near Field Magnetic Coupling (NFMC) for power and/or data transfer in an equivalent or smaller design volume by reducing conductor loss associated with increasing frequencies (due to the phenomenon referred to as Skin Effect). The proposed system also provides a solution that can be relatively easily achieved by existing manufacturing techniques (for example multi-layer printed wiring board), and can therefore be integrated with other circuit components such as ICs, resistors, capacitors, surface mount components, etc. Other advantages of the present system includes reducing power consumption thereby leading to longer battery lives (where applicable), a reduction in the Joule heating of the antenna, decreasing the consumption of environmental resources of the appliance/device, and any other benefit derived from a more energy efficient device.

Other applications that may benefit from these wireless systems include but are not limited to geo-sensing, oil exploration, fault detection, portable electronic, military, defense and medical devices, among other medical implantable, medical non-implantable, commercial, military, aerospace, industrial and other electronic equipment or device applications. It is understood that the scope of the invention covers not only any application that will benefit from increases in efficiency, but also any application that may require the use of an inductive element.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method for manufacturing a structure for wireless communication, the method comprising:
    a) creating a first resonator comprising a plurality of conductors, each conductor having a conductor length, a conductor width, a conductor thickness, and a conductor skin depth, wherein the conductor thickness is equal to or greater than a thickness of the skin depth so that an electrical resistance of each of the conductors is reduced when an electrical current is propagated therewithin, and wherein the plurality of conductors are arranged to form a resonator body having a resonator body length, a resonator body width and a resonator body thickness;
    b) forming an insulator between each of the plurality of conductors, wherein a thickness of the insulator is equal to or less than the conductor thickness; and
    c) forming at least one connection between two or more of the plurality of conductors.

2. The method of claim 1, wherein the conductor is formed as a conductor layer and the insulator is formed as an insulating layer.

3. The method of claim 2, wherein the conductor layer comprises at least one of a conductive tape, a conductive ribbon, and a deposited metal.

4. The method of claim 2, wherein the conductor is provided by at least one of a printed circuit board (PCB) process, physical vapor deposition, thin film processing techniques, and thick film processing techniques.

5. The method of claim 2, wherein the conductor layer is created by depositing through a mask.

6. The method of claim 2, further comprising a step of layering a plurality of conductor layers having the insulator between each of the conductor layers by placing a first conductive layer on top of a second conductive layer and separating the first conductive layer from the second conductive layer with a first insulator.

7. The method of claim 1, wherein the insulator layer is provided by at least one of a printed circuit board (PCB) process, physical vapor deposition, thin film processing techniques, and thick film processing techniques.

8. The method of claim 1, wherein the insulator layer is created by depositing through a mask.

9. The method of claim 1, wherein the step of forming the connection between two of the plurality of conductors further comprises the step of joining at least two of the conductors with at least one of a via, a solder, a tab, a wire, a pin, and a rivet.

10. The method of claim 1, wherein the conductor is formed from an electrically conductive material and the insulator is formed from an electrically insulative material.

11. The method of claim 10, wherein the electrically conductive material comprises at least copper, titanium, platinum and platinum/iridium alloys, tantalum, niobium, zirconium, hafnium, nitinol, Co—Cr—Ni alloys, stainless steel, gold, a gold alloy, palladium, carbon, silver, a noble metal, and a biocompatible material.

12. The method of claim 10, wherein the electrically insulative material comprises at least one air, Styrofoam, silicon dioxide, a biocompatible ceramic or any similar dielectric with a low permittivity, a non-conductive dielectric with a high permittivity, and a ferrite material.

13. The method of claim 1 further comprising the step of providing a circuit element selected from the group consisting of a resistor, an inductor and a capacitor, the circuit element being electrically connected to the resonator.

14. The method of claim 1, further comprising selecting the conductor thickness such that a current density is increased by at least 5 percent at a given operating frequency.

15. The method of claim 1, further comprising forming the conductor having at least one turn.

16. The method of claim 15, further comprising selecting a number of the plurality of conductors, a plurality of conductor thicknesses, a plurality of insulator thicknesses, the number of turns and a plurality of spaces within a turn or between turns such that a resulting parasitic capacitance is minimized at a given operating frequency.

17. The method of claim 1, further comprising selecting the resonator body thickness less than or equal to a radius of a resonator body structure.

18. A method for manufacturing a structure for wireless communication, the method comprising:
   a) creating a first resonator comprising a plurality of conductors, each conductor having a conductor length, a conductor width, a conductor thickness, and a conductor skin depth, wherein the conductor thickness is equal to or greater than a thickness of the skin depth so that an electrical resistance of each of the conductors is reduced from a first electrical resistance value to a lower second resistance value when an electrical current is propagated therewithin, and wherein the plurality of conductors are arranged to form a resonator body having a resonator body length, a resonator body width and a resonator body thickness less than or equal to a radius of the resonator body;
   b) forming an insulator between each of the plurality of conductors; and
   c) forming at least one connection between two or more of the plurality of conductors.

19. The method of claim 18, wherein the conductor is formed from an electrically conductive material and the insulator is formed from an electrically insulative material.

20. A method for manufacturing a structure for wireless communication, the method comprising:
   a) creating a first resonator having at least one turn comprising a plurality of conductors, each conductor having a conductor length, a conductor width, a conductor thickness, and a conductor skin depth, wherein the conductor thickness is equal to or greater than a thickness of the skin depth, and wherein the plurality of conductors are arranged to form a resonator body having a resonator body length, a resonator body width and a resonator body thickness;
   b) forming an insulator between each of the plurality of conductors, wherein a thickness of the insulator is equal to or less than the conductor thickness;
   c) forming at least one connection between two or more of the plurality of conductors; and
   d) selecting a number of the plurality of conductors, a plurality of conductor thicknesses, a plurality of insulator thicknesses, the number of turns and a plurality of spaces within the turn or between turns such that a resulting parasitic capacitance is minimized at a given operating frequency.

21. The method of claim 20, wherein the conductor is formed from an electrically conductive material and the insulator is formed from an electrically insulative material.

* * * * *